United States Patent
Camras et al.

(10) Patent No.: US 10,342,702 B2
(45) Date of Patent: Jul. 9, 2019

(54) APPARATUS AND METHOD FOR REDUCING INTRAOCULAR PRESSURE

(71) Applicant: CAMRAS VISION INC., Research Triangle Park, NC (US)

(72) Inventors: Lucinda Camras, Durham, NC (US); Rolf Erik Ypma, Durham, NC (US)

(73) Assignee: Camras Vision Inc., Research Triangle Park, NC (US)

( * ) Notice: Subject to any disclaimer, the term of this patent is extended or adjusted under 35 U.S.C. 154(b) by 612 days.

(21) Appl. No.: 14/826,866

(22) Filed: Aug. 14, 2015

(65) Prior Publication Data

US 2016/0058616 A1 Mar. 3, 2016

Related U.S. Application Data

(63) Continuation-in-part of application No. 14/473,228, filed on Aug. 29, 2014, now Pat. No. 10,201,451.

(51) Int. Cl.
 *A61F 9/007* (2006.01)
(52) U.S. Cl.
 CPC .. *A61F 9/00781* (2013.01); *A61F 2250/0024* (2013.01)
(58) Field of Classification Search
 CPC .................... A61F 9/00781; A61F 2250/0024
 USPC ........ 604/7-10, 264, 30, 6.09, 6.1; 606/153, 606/108
 See application file for complete search history.

(56) References Cited

U.S. PATENT DOCUMENTS

| 3,788,327 A | 1/1974 | Donowitz et al. |
| 4,886,488 A | 12/1989 | White |
| 5,041,081 A | 8/1991 | Odrich |
| 5,127,901 A | 7/1992 | Odrich |

(Continued)

FOREIGN PATENT DOCUMENTS

| EP | 2 896 386 A1 | 7/2015 |
| WO | 2009/105573 A1 | 8/2009 |

(Continued)

OTHER PUBLICATIONS

International Search Report mailed in PCT/US17/40738 dated Nov. 2, 2017, 4 pages.

(Continued)

*Primary Examiner* — Leslie R Deak
(74) *Attorney, Agent, or Firm* — McDonnell Boehnen Hulbert & Berghoff LLP

(57) ABSTRACT

An apparatus for reducing/stabilizing intraocular pressure is provided. A tube extends from an inlet end in fluid communication with an anterior chamber of the eye, to direct an aqueous humor flow from the anterior chamber to an outlet end in fluid communication with a cavity, defined by a housing, for receiving the aqueous humor. A flow control device is operably engaged with the housing, and is configured to control the flow of the aqueous humor, via a conduit defined thereby and extending from the cavity, to a location away from the anterior chamber. The conduit is dilatable in response to the intraocular pressure being above a preselected pressure, to increase the flow or to decrease resistance to flow of the aqueous humor through the conduit to the drainage site and to reduce the intraocular pressure to no greater than the preselected pressure. Associated apparatuses and methods are also provided.

37 Claims, 20 Drawing Sheets

(56) References Cited

U.S. PATENT DOCUMENTS

| | | | |
|---|---|---|---|
| 5,171,213 A | 12/1992 | Price, Jr. | |
| 5,300,020 A | 4/1994 | L'Esperance, Jr. | |
| 5,346,464 A | 9/1994 | Camras | |
| 5,626,558 A | 5/1997 | Suson | |
| 5,656,026 A | 8/1997 | Joseph | |
| 5,743,868 A | 4/1998 | Brown et al. | |
| 5,807,302 A | 9/1998 | Wandel | |
| 5,830,173 A | 11/1998 | Avery et al. | |
| 5,882,327 A | 3/1999 | Jacob | |
| 6,077,299 A | 6/2000 | Adelberg et al. | |
| 6,261,256 B1 | 7/2001 | Ahmed | |
| 6,537,241 B1 | 3/2003 | Odland | |
| 6,544,208 B2 | 4/2003 | Ethier et al. | |
| 6,558,342 B1 | 5/2003 | Yaron et al. | |
| 6,595,945 B2 | 7/2003 | Brown | |
| 6,881,198 B2 | 4/2005 | Brown | |
| 7,118,547 B2 | 10/2006 | Dahan | |
| 7,135,009 B2 | 11/2006 | Tu et al. | |
| 7,156,821 B2 | 1/2007 | Dohlman | |
| 7,186,233 B2 | 3/2007 | Dohlman | |
| 7,192,412 B1 | 3/2007 | Zhou et al. | |
| 7,458,953 B2 | 12/2008 | Peyman | |
| 7,641,627 B2 | 1/2010 | Camras et al. | |
| 7,670,310 B2 | 3/2010 | Yaron et al. | |
| 8,579,848 B2 | 11/2013 | Field et al. | |
| 8,628,492 B2 | 1/2014 | Lin et al. | |
| 8,632,489 B1 | 1/2014 | Ahmed | |
| 8,753,305 B2 | 6/2014 | Field et al. | |
| 8,986,240 B2 | 3/2015 | Dos Santos et al. | |
| 8,998,838 B2 | 4/2015 | Yalamanchili | |
| 9,072,588 B2 | 7/2015 | Böhm et al. | |
| 9,101,445 B2 | 8/2015 | Bigler et al. | |
| 9,132,034 B2 | 9/2015 | Dos Santos | |
| 9,155,653 B2 | 10/2015 | Field | |
| 9,186,274 B2 | 11/2015 | Camras et al. | |
| 9,226,851 B2 | 1/2016 | Gunn | |
| 9,259,353 B2 | 2/2016 | Dos Santos et al. | |
| 9,333,115 B2 | 5/2016 | Dos Santos | |
| 9,339,187 B2 | 5/2016 | Rickard | |
| 9,381,301 B2 | 7/2016 | Lattanzio et al. | |
| 9,456,924 B2 | 10/2016 | Noroozi et al. | |
| 9,492,321 B2 | 11/2016 | Gunn et al. | |
| 9,572,712 B2 | 2/2017 | Gunn | |
| 9,622,910 B2 | 4/2017 | Field et al. | |
| 9,681,983 B2 | 6/2017 | Lind | |
| 2002/0143284 A1 | 10/2002 | Tu et al. | |
| 2002/0169468 A1 | 11/2002 | Brown | |
| 2004/0073156 A1 | 4/2004 | Brown | |
| 2004/0127843 A1 | 7/2004 | Tu et al. | |
| 2004/0215126 A1 | 10/2004 | Ahmed | |
| 2004/0249441 A1 | 12/2004 | Miller et al. | |
| 2004/0254521 A1 | 12/2004 | Simon | |
| 2005/0049578 A1 | 3/2005 | Tu et al. | |
| 2005/0119737 A1 | 6/2005 | Bene et al. | |
| 2005/0240142 A1 | 10/2005 | Dohlman | |
| 2005/0240143 A1 | 10/2005 | Dohlman | |
| 2006/0036207 A1 | 2/2006 | Koonmen et al. | |
| 2006/0069340 A1* | 3/2006 | Simon | A61F 9/00781 604/8 |
| 2006/0116626 A1 | 6/2006 | Smedley et al. | |
| 2006/0189915 A1 | 8/2006 | Camras | |
| 2006/0235367 A1 | 10/2006 | Takashima et al. | |
| 2007/0004998 A1 | 1/2007 | Rodgers et al. | |
| 2007/0156079 A1 | 7/2007 | Brown | |
| 2007/0254005 A1 | 11/2007 | Pathak et al. | |
| 2008/0228127 A1 | 9/2008 | Burns et al. | |
| 2009/0036818 A1 | 2/2009 | Grahn et al. | |
| 2009/0117166 A1 | 5/2009 | Myung et al. | |
| 2009/0326432 A1 | 12/2009 | Schmidt et al. | |
| 2010/0056979 A1 | 3/2010 | Smedley et al. | |
| 2010/0057055 A1 | 3/2010 | Camras et al. | |
| 2010/0114006 A1 | 5/2010 | Baerveldt | |
| 2011/0071456 A1 | 3/2011 | Rickard | |
| 2011/0105986 A1 | 5/2011 | Bronstein et al. | |
| 2012/0302861 A1 | 11/2012 | Marshall et al. | |
| 2013/0096483 A1 | 4/2013 | Dacquay | |
| 2013/0150775 A1 | 6/2013 | Dos Santos et al. | |
| 2013/0150776 A1 | 6/2013 | Böhm et al. | |
| 2013/0150777 A1 | 6/2013 | Böhm et al. | |
| 2013/0150778 A1 | 6/2013 | Dos Santos | |
| 2013/0150779 A1 | 6/2013 | Field | |
| 2013/0218064 A1 | 8/2013 | Rickard | |
| 2013/0317412 A1 | 11/2013 | Dacquay et al. | |
| 2013/0317413 A1 | 11/2013 | Field et al. | |
| 2014/0005587 A1 | 1/2014 | Gelvin et al. | |
| 2014/0066832 A1 | 3/2014 | Ovchinnikov et al. | |
| 2014/0081195 A1 | 3/2014 | Clauson | |
| 2014/0163448 A1 | 6/2014 | Lind et al. | |
| 2014/0171777 A1 | 6/2014 | Sanchez et al. | |
| 2015/0045716 A1 | 2/2015 | Gallardo Inzunza | |
| 2015/0057595 A1 | 2/2015 | Gunn et al. | |
| 2015/0057596 A1 | 2/2015 | Lind et al. | |
| 2015/0057597 A1 | 2/2015 | Johnson et al. | |
| 2015/0202082 A1 | 7/2015 | Ilios et al. | |
| 2015/0230983 A1 | 8/2015 | Johnson | |
| 2015/0230984 A1 | 8/2015 | Gunn | |
| 2015/0257931 A1 | 9/2015 | Sanchez et al. | |
| 2015/0265469 A1 | 9/2015 | Olson et al. | |
| 2016/0033270 A1 | 3/2016 | Camras et al. | |
| 2016/0058615 A1 | 3/2016 | Camras et al. | |
| 2016/0058616 A1 | 3/2016 | Camras et al. | |
| 2016/0067092 A1 | 3/2016 | Lind et al. | |
| 2016/0235298 A1 | 8/2016 | Gunn | |
| 2016/0242962 A1 | 8/2016 | Torello et al. | |
| 2016/0296371 A1 | 10/2016 | Gelvin | |
| 2017/0348148 A1 | 12/2017 | Bigler et al. | |
| 2017/0348149 A1 | 12/2017 | Stergiopulos et al. | |
| 2018/0078416 A1 | 3/2018 | Christiansen | |
| 2018/0092774 A1 | 4/2018 | Mehta | |

FOREIGN PATENT DOCUMENTS

| | | |
|---|---|---|
| WO | 2013/155252 A1 | 10/2013 |
| WO | 2014/036437 A1 | 3/2014 |
| WO | 2014/130574 A1 | 8/2014 |
| WO | 2016/100500 A1 | 6/2016 |
| WO | 2017/059272 A1 | 4/2017 |
| WO | 2017/106517 A1 | 6/2017 |
| WO | 2018/009556 A1 | 1/2018 |

OTHER PUBLICATIONS

International Search Report mailed in PCT/US16/054828 dated Dec. 13, 2016, 1 page.

International Search Report and Written Opinion mailed in PCT/US18/029717 dated Sep. 21, 2018, 20 pages.

Dohlman et al., "Shunts to Divert Aqueous Humor to Distant Epithelialized Cavities After Keratoprosthesis Surgery", Glaucoma, 2010, 19(2), 111-115.

Molteno et al., "Otago Glaucoma Surgery Outcome Study: Factors Controlling Capsule Fibrosis around Molteno Implants with Histopathological Correlation", The American Academy of Opthalmology, 2003, 110(11), 2198-2206.

* cited by examiner

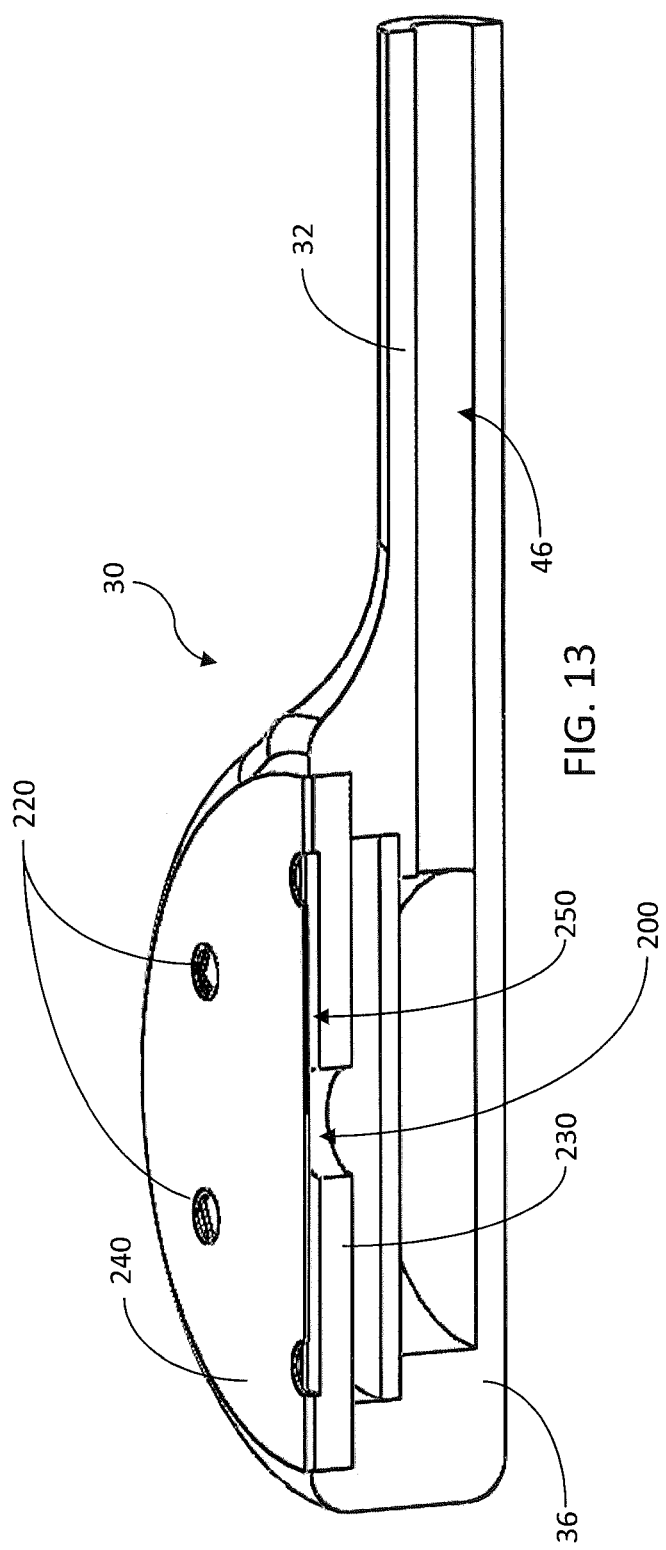

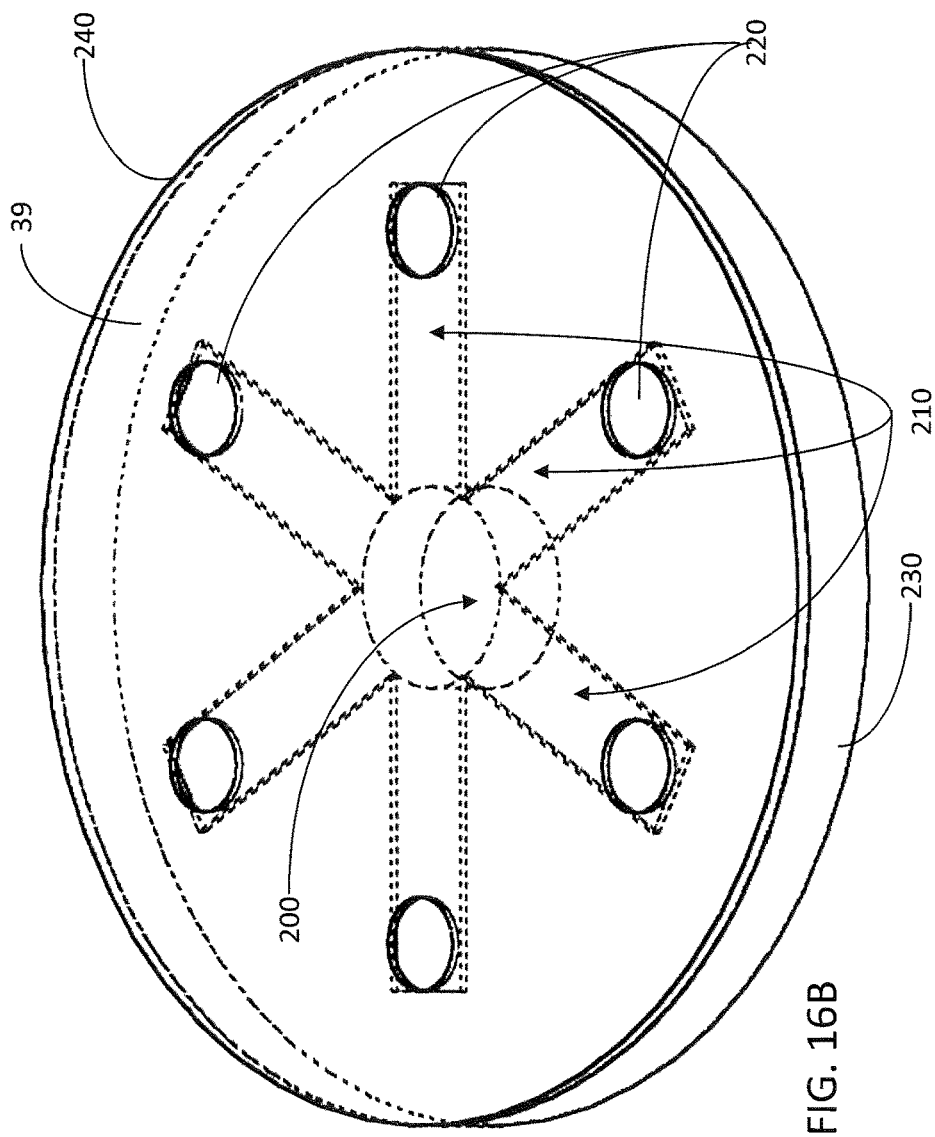

APPARATUS AND METHOD FOR REDUCING INTRAOCULAR PRESSURE

CROSS-REFERENCE TO RELATED APPLICATIONS

The present patent application is a continuation-in-part of U.S. patent application Ser. No. 14/473,228, filed Aug. 29, 2014, the disclosure of which is incorporated herein by reference in its entirety.

BACKGROUND

Field of the Disclosure

Aspects of the present disclosure are generally directed to an apparatus and method for draining aqueous humor from an anterior chamber of an eye to a location external or distal to the anterior chamber for reducing intraocular pressure and, more particularly, to an implantable apparatus for regulating intraocular pressure using a flow control device having an dilatable conduit for directing a flow of the aqueous humor externally of the anterior chamber of the eye to an external or distal drainage site for reducing and regulating intraocular pressure.

Description of Related Art

Glaucoma is a group of chronic optic nerve diseases and a leading cause of irreversible blindness. The major risk factor in glaucoma is elevated intraocular pressure due to improper drainage of aqueous humor from the eye. Reduction of intraocular pressure is the only proven treatment to stop the progression of vision loss by reducing stress on the optic nerve.

Standard glaucoma surgeries to reduce intraocular pressure, such as trabeculectomies and glaucoma drainage device implantation, tend to be lengthy and traumatic with unpredictable outcomes and complication rates of 20-60%. Implantable drainage devices function to drain excess aqueous humor from the eye, and installation of such a drainage device typically requires a surgical opening made in the sclera to reach the interior of the eye, in particular the anterior chamber or the posterior chamber. The drainage device is then inserted into the interior of the eye for conducting the aqueous humor to the subconjunctival space (with such a device herein referred to as a subconjunctival shunt), or externally of the conjunctiva (with such a device herein referred to as an external shunt).

A problem associated with subconjunctival shunts is potential scarring of the bleb in the subconjunctival space affecting its fibrous capsule formation around the outlet, which in many cases requires surgical revision that leads to additional risk of complications. Therefore, there is an ongoing search to identify and utilize alternate drainage sites to avoid many problems associated with bleb and fibrous capsule formations.

External shunts avoid bleb and fibrous capsule formation and the unpredictability of wound healing in the subconjunctival space. However, the outlet of an external shunt may be perceived by the patient as a foreign body, especially those that lie on the corneal surface. These shunts can also be displaced by local tissue motion or extruded by constrictive wound healing processes. In addition, external shunts can expose a mechanical conduit available to transmit microorganisms from the outside to the interior of the eye, potentially leading to retrograde infection.

All drainage devices implanted in the eye have the potential to clog from proteins or other substances in the aqueous humor. Clogging reduces permeability of the device and may lead to elevation of intraocular pressure compared to baseline. Moreover, the intraocular pressure may naturally vary or fluctuate due to changes in aqueous humor dynamics of the particular eye, regardless of the effect of a drainage device.

For the foregoing reasons there is a need for an improved drainage device for directing aqueous humor away from the anterior chamber of an eye for reducing and managing intraocular pressure.

SUMMARY OF THE DISCLOSURE

The above and other needs are met by aspects of the present disclosure which, in one aspect, provides an apparatus for draining aqueous humor from an eye for reducing or stabilizing intraocular pressure, wherein the eye includes an anterior chamber, a cornea, a surrounding marginal limbus by which the cornea is continuous with a scleral layer and a conjunctival layer, and an external ocular surface of the eye under an eyelid. Such an apparatus may comprise a tube extending between an inlet end and an outlet end, with the inlet end being adapted to be in fluid communication with the anterior chamber of the eye, and with the tube being adapted to direct a flow of aqueous humor from the anterior chamber and through the inlet end to the outlet end. A housing defines a cavity in fluid communication with the outlet end of the tube, wherein the cavity is configured to receive the aqueous humor. A flow control device is operably engaged with the housing and is configured to control the flow of the aqueous humor from the cavity to a location external or distal to the anterior chamber. The flow control device defines a conduit in communication between the cavity and the external location, wherein the conduit is dilatable in response to the intraocular pressure being above a preselected pressure, to increase the flow or to decrease resistance to flow of the aqueous humor through the conduit to the external location and to reduce the intraocular pressure to no greater than the preselected pressure.

Another aspect of the present disclosure provides a method of manufacturing an apparatus for draining aqueous humor from an eye for reducing or stabilizing intraocular pressure, wherein the eye includes an anterior chamber, a cornea, a surrounding marginal limbus by which the cornea is continuous with a scleral layer and a conjunctival layer, and an external ocular surface of the eye under an eyelid. Such a method comprises engaging an outlet end of a tube into fluid communication with a cavity defined by a housing, with the outlet end extending to an inlet end adapted to be in fluid communication with the anterior chamber of the eye, and with the tube being adapted to direct the flow of aqueous humor from the anterior chamber and through the inlet end and to the outlet end such that the aqueous humor is received by the cavity. A dilatable flow control device is engaged with the housing, wherein the dilatable flow control device is adapted to control a flow of the aqueous humor from the cavity to a location external or distal to the anterior chamber, and wherein the flow control device defines a conduit in communication between the cavity and the external location, the conduit being dilatable in response to the intraocular pressure being above a preselected pressure, to increase the flow or to decrease resistance to flow of the aqueous humor through the conduit to the external location and to reduce the intraocular pressure to no greater than the preselected pressure.

Still another aspect of the present disclosure provides an apparatus for draining aqueous humor from an eye for reducing or stabilizing intraocular pressure, wherein the eye includes an anterior chamber, a cornea, a surrounding marginal limbus by which the cornea is continuous with a scleral layer and a conjunctival layer, and an external ocular surface of the eye under an eyelid. Such an apparatus comprises a tube extending between an inlet end and an outlet end, with the inlet end being adapted to be in fluid communication with the anterior chamber of the eye, and with the tube being adapted to direct a flow of aqueous humor from the anterior chamber and through the inlet end to the outlet end. A flow control device is operably engaged with the outlet end and is configured to control the flow of the aqueous humor from the tube to a location external to the anterior chamber. The flow control device defines a conduit in communication between the outlet end and the external location, wherein the conduit is dilatable in response to the intraocular pressure being above a preselected pressure, to increase the flow or to decrease resistance to flow of the aqueous humor through the conduit to the external location and to reduce the intraocular pressure to no greater than the preselected pressure. A first filter device is disposed in fluid communication between the inlet end of the tube and the flow control device, wherein the filter device is configured to filter contaminants from the aqueous humor prior to the flow control device. A second filter device is disposed in fluid communication with the flow control device, opposite to the outlet end of the tube from the flow control device, wherein the second filter device is configured to filter contaminants from any backflow to the flow control device.

Further features and advantages of the present disclosure are set forth in more detail in the following description.

BRIEF DESCRIPTION OF THE DRAWINGS

For a more complete understanding of the present invention, reference should now be had to the embodiments shown in the accompanying drawings and described below. In the drawings:

FIG. 13 schematically illustrates a cutaway view of a drainage device, according to one embodiment of the present disclosure;

FIGS. 16A and 16B schematically illustrate configurations of two-piece flow control device for a drainage device, according to various embodiments of the present disclosure;

DETAILED DESCRIPTION

The present disclosure now will be described more fully hereinafter with reference to the accompanying drawings, in which some, but not all aspects of the disclosure are shown. Indeed, the disclosure may be embodied in many different forms and should not be construed as limited to the aspects set forth herein; rather, these aspects are provided so that this disclosure will satisfy applicable legal requirements. Like numbers refer to like elements throughout.

Certain terminology is used herein for convenience only and is not to be taken as a limitation on the scope of the disclosure. For example, words such as "upper," "lower," "left," "right," "horizontal," "vertical," "upward," and "downward" merely describe the configuration shown in the figures. Indeed, the components may be oriented in any direction and the terminology, therefore, should be understood as encompassing such variations unless specified otherwise.

Figure 1:
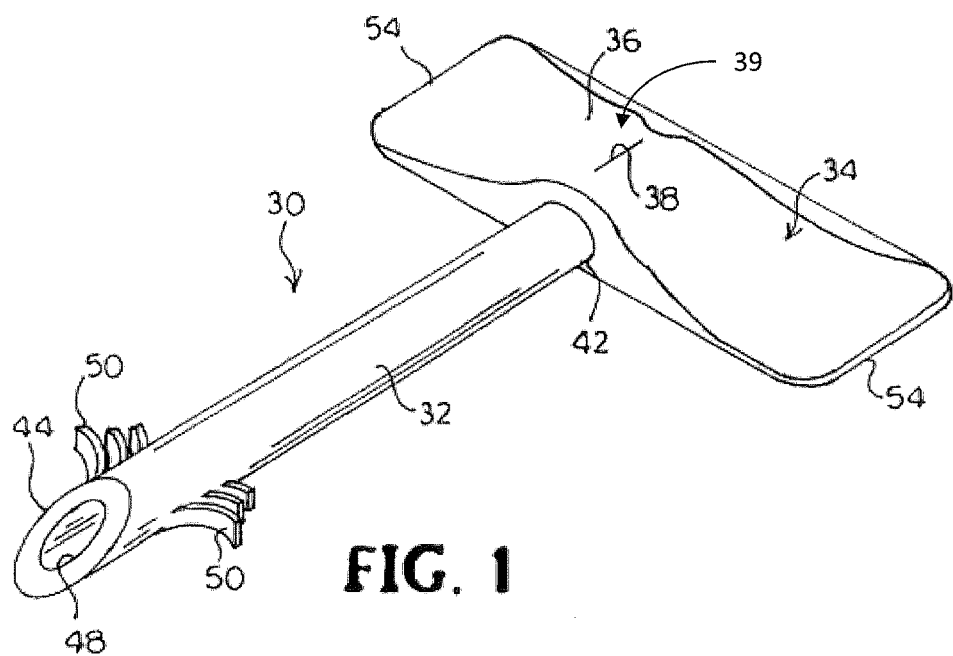
FIG. 1 is a perspective view of an embodiment of a drainage device for reducing intraocular pressure.

FIG. 1 schematically illustrates an implantable ocular drainage device, generally designated as element 30, according to one aspect of the present disclosure. The drainage device 30 comprises a tubular body 32 and an outlet assembly 34. The tubular body 32 includes an inlet end 44 and a longitudinally-opposed outlet end 42, and is configured to direct a fluid between the inlet 44 and outlet 42 ends. At least a portion of the tubular body 32 of the drainage device 30 is implantable into the anterior chamber of an eye for draining aqueous humor therefrom (see, e.g., FIGS. 4 and 5).

The tubular body 32 of the drainage device 30 is substantially cylindrical and hollow, and has a proximal (outlet) end 42 and a distal (inlet) end 44. The tubular body 32 defines a lumen 46 that extends between the proximal end 42 and the distal end 44 with the distal end defining at least one opening 48 communicating with the lumen 46. The at least one opening 48 is configured to provide a fluid inlet at the distal end 44 of the tubular body 32. In some aspects, the distal end 44 of the tubular body 32 may be beveled for facilitating entry of the distal end 44 into the anterior chamber or other portion of the eye.

The lumen 46 forms at least a portion of a flow path that permits the drainage of aqueous humor from the anterior chamber of the eye to a location external to the anterior chamber. For example, the external location (to the anterior chamber) may be an external ocular surface of the eye. In other instances, the external location may include another chamber within the eye, the subconjunctival space, the suprachoroidal space, or the like. In one aspect, the tubular body 32 has a length sufficient to provide fluid communication between the anterior chamber of the eye and the fornix or cul-de-sac region under the eyelid to allow aqueous humor to flow from the anterior chamber through the lumen 46 and into the tear film associated with the eye when the drainage device 30 is implanted in or attached to the eye. For this purpose, the tubular body 32 of the drainage device 30 may have a minimum length, for example, of at least about 3 mm for the outlet assembly 34 to be positioned about the fornix or cul-de-sac region under the eyelid. In one aspect, the tubular body 32 may have a length of between about 4 mm and about 9 mm for adult humans. In use, the tubular body 32 may lie substantially underneath the conjunctiva with the distal (input) end disposed in the anterior (or posterior) chamber of the eye (see, e.g., FIGS. 4 and 5). One skilled in the art will appreciate, however, that the dimensions and deployment location of the drainage device 30 may vary considerably depending on the location to which the aqueous humor drained from the anterior chamber is directed.

The transverse/lateral cross-sectional shape of the tubular body 32, in addition to circular as shown in FIGS. 1-5, may be other suitable shapes such as, for example, oval, square, trapezoidal, rectangular, or any combination thereof. Regardless of shape, the cross-sectional size of the lumen 46 defined by the tubular body 32 may vary to selectively alter the fluid flow characteristics of the aqueous humor. For example, a relatively small cross-sectional size can be used to restrict the fluid flow of the aqueous humor. In one aspect, the cross-sectional dimension of the lumen 46 may range, for example, from about 0.05 mm to about 1.0 mm.

One or more barbs 50 may be provided adjacent the distal end 44 of the tubular body 32. The barbs 50 can extend from a portion of the outer surface of the tubular body 32 for contact with the sclera when the drainage device 30 is implanted or engaged with the eye. The barbs 50 are adapted to engage the sclera and provide stability until biointegration of the tubular body 32 in the subconjunctival space. The barbs 50 may be formed as part of the tubular body 32 of the drainage device 30 during manufacture or may be subsequently fused or bonded to the tubular body 32 in an appropriate manner.

Figure 3:
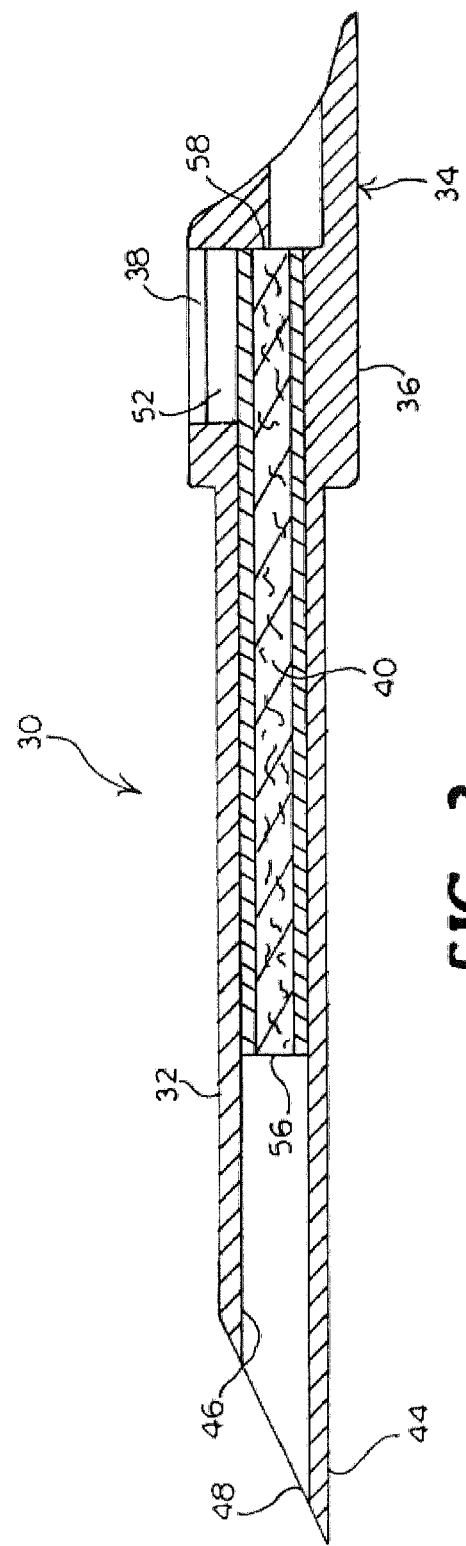
FIG. 3 is a longitudinal cross-section elevation view of the drainage device as shown in FIG. 1.

Referring to FIG. 3, the head portion 36 of the outlet assembly 34 defines an interior cavity 52. The head portion 36 is integral with, or attached to, the proximal (outlet) end 42 of the tubular body 32 such that the cavity 52 is in fluid communication with the lumen 46 of the tubular body 32 so as to receive a flow of the aqueous humor therefrom. In the illustrated aspect, the head portion 36 and the tubular body 32 may be formed integrally as a single unit. Alternatively, each component may be formed separately from the other. The head portion 36 may be dome-shaped (or convex) to provide a substantially continuous transition surface from along an outer surface of the head portion 36 to the surface of the eye (i.e., the convex curvature is configured to make a smooth transition to the surface of the eye). Such a configuration/shape of the head portion 36 may be better tolerated by the patient, if the head portion does not feel like a foreign object in the eye in relation to the eyelid. One skilled in the art will appreciate, however, that other shapes of the head portion 36 may be suitable and appropriate for providing similar sensory perception for the user. For example, a minimally protruding, substantially flat head portion 36 with rounded edges may be equally well tolerated. Other appropriate designs may be determined by those skilled in the art. The inner (convex) surface of the head portion 36 may be flat or curved (or a combination of both), as appropriate, to correspond to the shape of the external surface of the sclera where the drainage device 30 is to be positioned.

The head portion 36 may further comprise integral tabs 54 extending outward from an axis extending through the drainage device 30. Alternatively, the tabs 54 may be separately-formed pieces attached to the head portion 36. If the tabs 54 are separately-formed pieces, the tabs 54 may be comprised of a flexible biocompatible material, such as silicone or polyurethane, which may be readily deformable in compliance with eye movement. As further disclosed herein, the tabs 54 may function to stabilize the position of the drainage device 30 (i.e., by way of the head portion 36) with respect to the eye, and may thus prevent extrusion of the drainage device 30 from its intended location with respect to the eye, while also possibly reducing ocular surface irritation and/or conjunctival erosion.

In some aspects, the drainage device 30 may comprise a filter 40 and/or a flow control device 39 for maintaining and/or controlling intraocular pressure and for allowing for a more physiological dynamic of the aqueous humor. In such aspects, the head portion 36 of the outlet assembly 34 may be configured to house the flow control device 39, or may otherwise define an opening for receiving the flow control device 39, through which opening the filter 40 may be inserted into and/or removed from the head portion 36.

Figure 2:
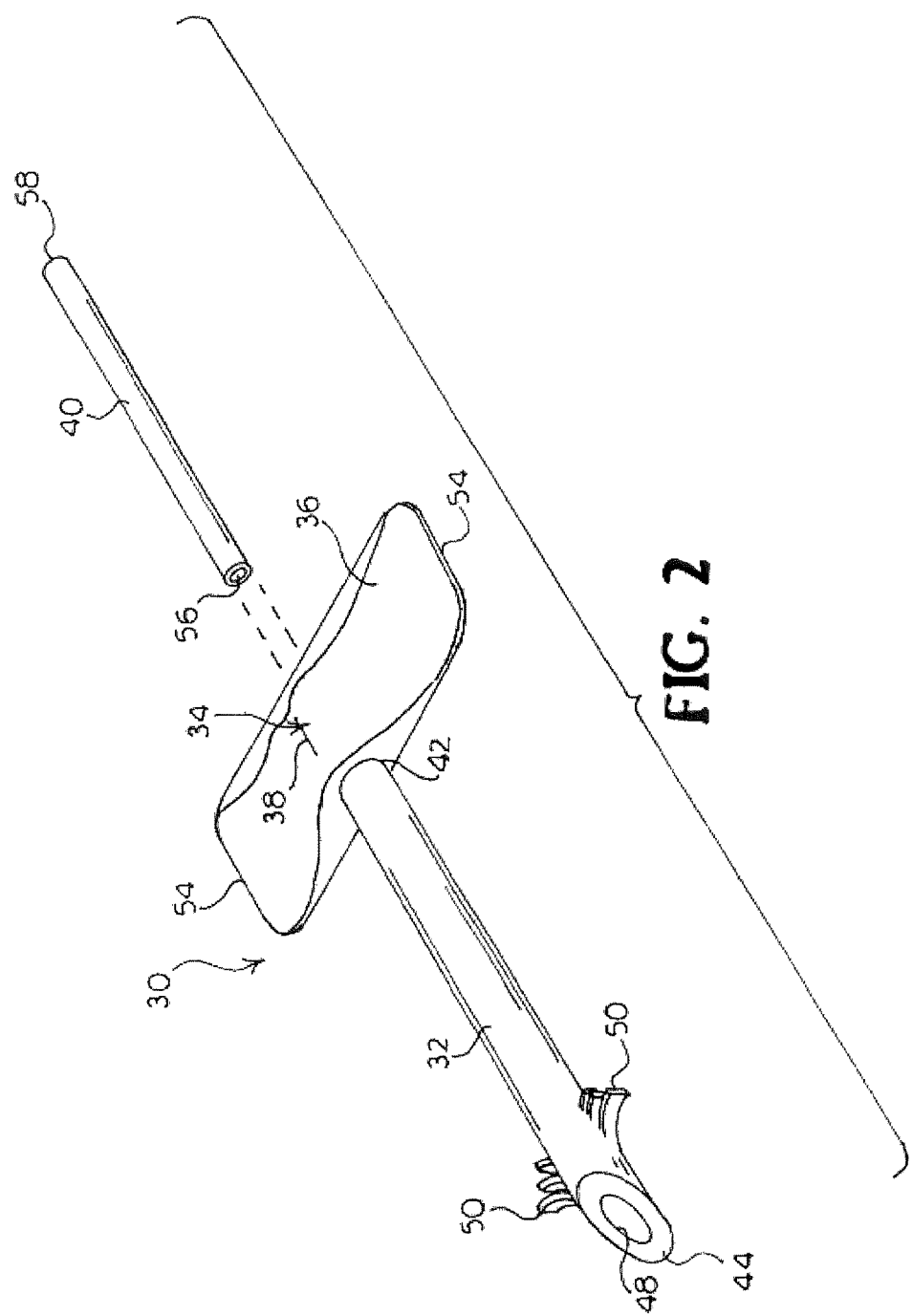
FIG. 2 is an exploded perspective view of the drainage device as shown in FIG. 1.

FIGS. 2 and 3 schematically illustrate, for example, a filter 40 at least partially disposed within the head portion 36 and the lumen 46 at the proximal end 42 of the tubular body 32 of the drainage device 30. In one aspect, the filter 40 may be configured as an elongate member having a distal inflow end 44 and a proximal outflow end 42. As shown in FIG. 3, for example, the filter 40 may be configured to extend laterally across the lumen 46 such that the lumenal passage of the tubular body 32 is closed or substantially closed by the filter 40. The aqueous humor flowing through the lumen 46 is therefore directed through the filter 40, wherein the filter 40 filters the aqueous humor to prevent bacterial migration in either direction along the lumen. The filter 40 may also be configured to regulate or at least facilitate the regulation of intraocular pressure by providing a predetermined resistance to outflow of aqueous humor from the anterior chamber of the eye to the external location (i.e., into the tear film about the exterior surface of the eye). In some aspects the filter 40 may be configured as a resistive component for the flow of aqueous humor. That is, the filter can provide particular flow rate of aqueous humor by selecting filter characteristics such as a predetermined number and size of pores and a selected overall length of the filter 40 (i.e., the flow path). These parameters, either separately or in combination, may be configured to provide an appropriate resistance to the flow of aqueous humor sufficient to reduce and maintain intraocular pressure, while preventing ocular hypotony. The filter 40 may have a gradient of pore sizes along the length of the filter 40. For example, the pore size may continually decrease from the distal end 44 of the filter 40 to the proximal end 42 in order to prevent debris accumulation at the distal (inlet) end 44 of the filter 40. Larger pores sizes at the distal end 44 and at the proximal end 42 of the filter 40 may provide a pore gradient, which may help to reduce the effect of clogging on the outflow resistance.

In some aspects, the filter 40 may be removable and replaceable, and may be facilitated by external access to the outlet assembly 34, without disrupting the position of the drainage device 30 in the eye (i.e., the tubular body 32). By replacing the filter 40, for example, the ocular pressure can be regulated by selecting a filter configuration that provides a selected aqueous humor flow rate. Alternatively, the filter 40 may be configured to form a permanent element of the drainage device 30.

In some aspects, a flow control device 39 may be housed by, in fluid communication with, or otherwise operably engaged with the head portion 36 (i.e., a housing defined and provided by the head portion 36). If the filter 40 is implemented in such aspects, the filter 40 may be disposed in fluid communication between the inlet (distal) end 44 of the tubular body 32 and the flow control device 39, with the filter 40 being configured to filter contaminants from the aqueous humor prior to the flow control device 39. In other instances, the filter 40 may be engaged with the housing of the head portion 36 subsequent to the outlet (proximal) end 42 of the tubular body (or "tube") 30, and wherein the housing of the head portion 36 is configured such that the flow control device 39 operably engaged therewith is removable or replaceable with respect to the housing, so as to allow the filter 40 to be removed or replaced. In still other aspects, the filter 40 may be disposed in fluid communication with the flow control device 39, opposite to the outlet (proximal) end 42 of the tubular body 32 from the flow control device 39, wherein the filter 40 is configured to filter contaminants from any backflow to the flow control device 39. In such instances, the filter 40 may be engaged with the housing of the head portion 36 subsequent to the flow control device 39, and wherein the housing may be configured such that the filter 40 engaged therewith is removable or replaceable with respect to the housing.

In some instances, the head portion/housing 36 may be configured to define a cavity 52 therein, wherein the flow control device 39 may be configured to control a flow of the aqueous humor from the cavity 52 to the external ocular surface of the eye. In some particular aspects, the flow control device 39 defines a conduit 38 in communication between the cavity 52 and the external ocular surface. In some instances, the flow control device 39 may comprise a relatively thin and flexible membrane defining a conduit 38 in the form of an elongate slit (see, e.g., FIGS. 1 and 2), wherein the flexible membrane is configured to deform about a medial portion along the length of the slit, in response to elevated intraocular pressure, to allow aqueous humor to exit the drainage device 30. In other aspects, such as shown, for example, in FIGS. 6A, 14, 15A, and 15B, the flow control device 39 may comprise an elongate or relatively thick portion defining a conduit 38 extending through the thickness. In particular instances, the conduit 38 is dilatable in response to the intraocular pressure being above a preselected or threshold pressure, to increase the flow or to decrease resistance to flow of the aqueous humor through the conduit 38 to the external location (i.e., the external ocular surface) and to reduce and/or stabilize the intraocular pressure to no greater than the preselected pressure. For example, the configuration of the dilatable conduit 38 may be determined according to a preselected intraocular pressure, wherein the preselected ocular pressure may be a factor of, for example, the patient's age, physical characteristics, characteristics of the eye, advancement of the condition, particular physiological dynamics, or the like that are particular to a particular patient. The lateral cross-section of the conduit 38 may take different forms such as, for example, circular, ovular, square, rectangular, or any other suitable shape, whether regular or irregular.

Figure 6A:
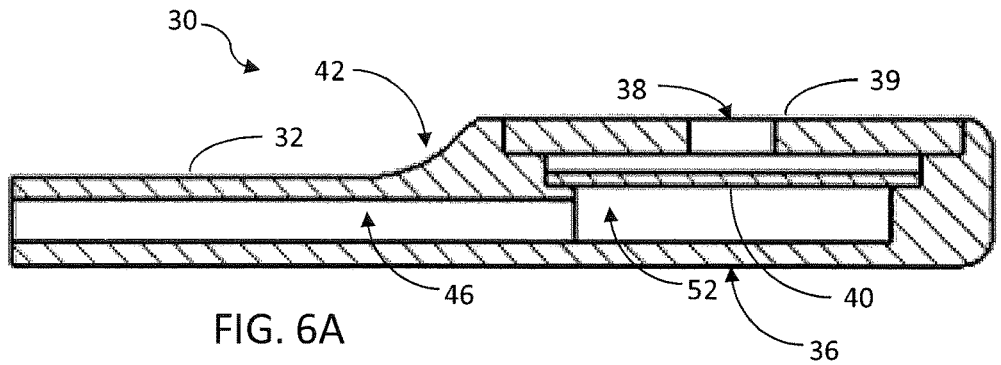
FIGS. 6A-6C schematically illustrate a drainage device, according to various embodiments of the present disclosure
Figure 6B:
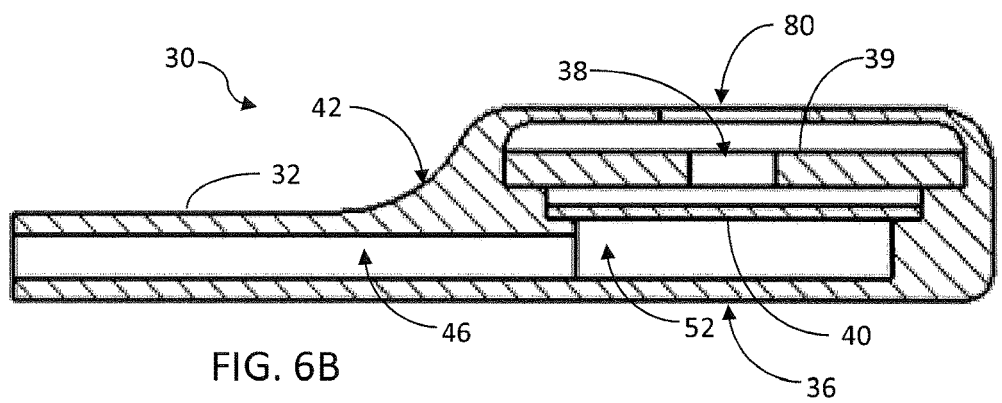
Figure 6C:
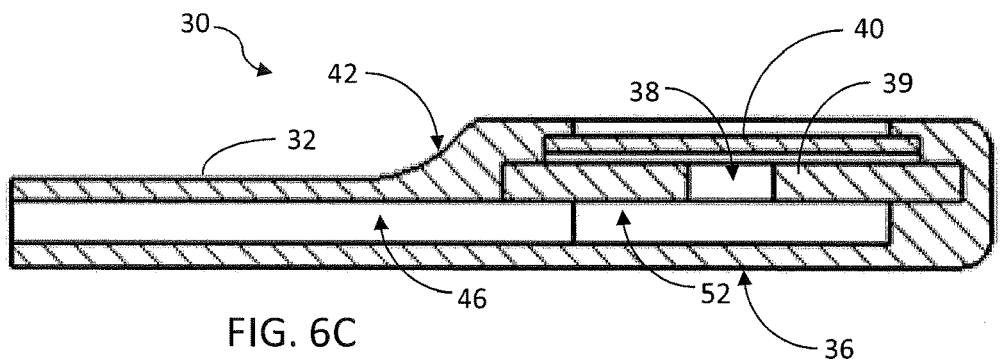
Figure 7:
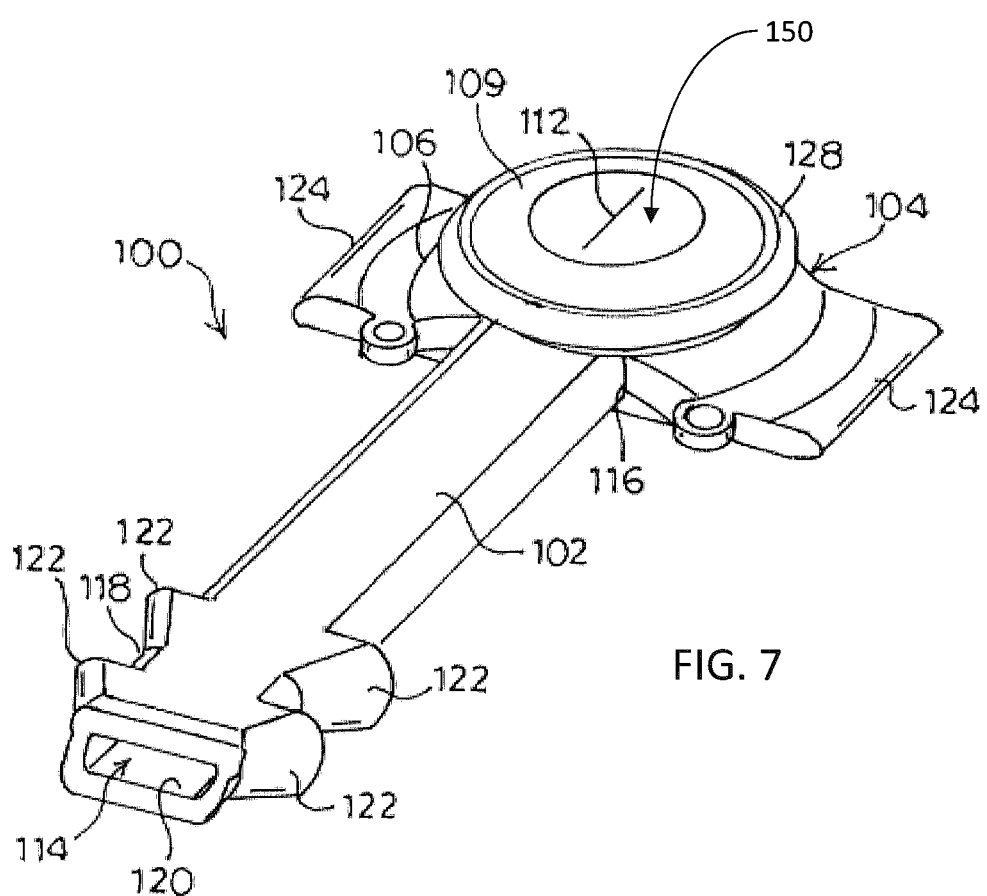
FIG. 7 is a perspective view of an alternate embodiment of a drainage device for reducing intraocular pressure.
Figure 8:
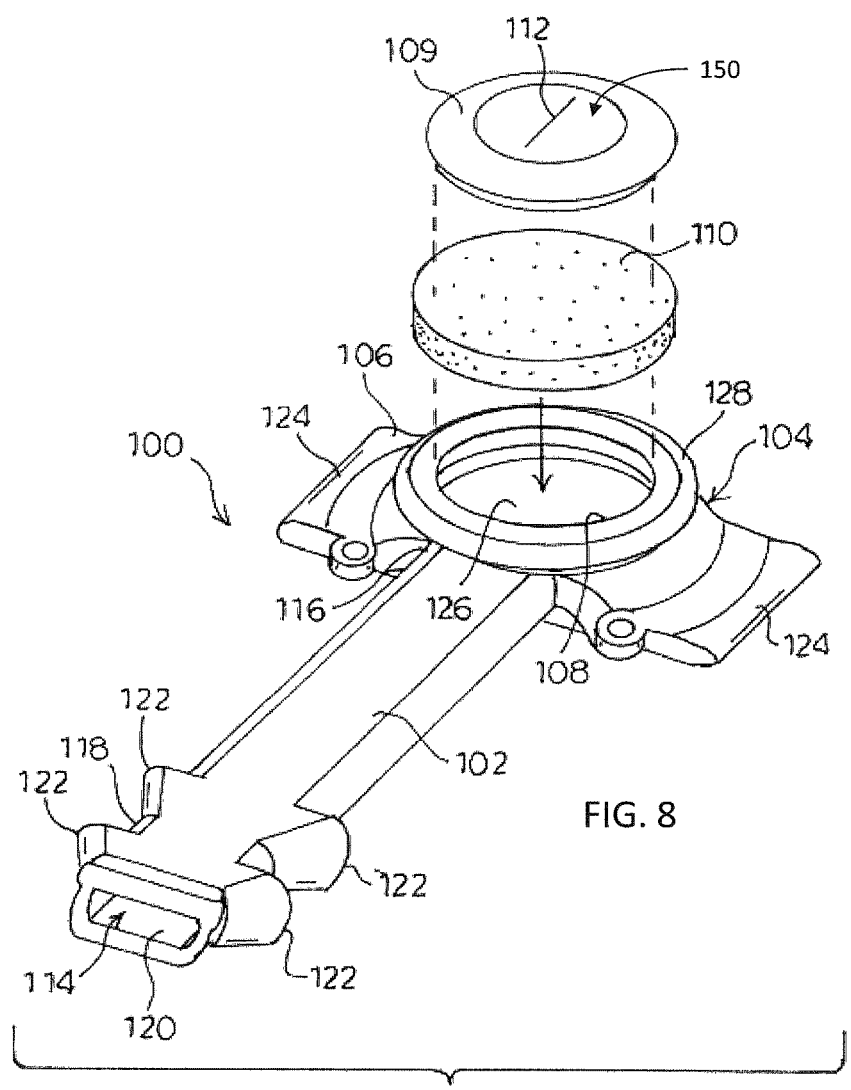
FIG. 8 is an exploded perspective view of the drainage device as shown in FIG. 7.

In some aspects, as shown in FIG. 6B, the flow control device 39 may be disposed within the cavity 52 defined by the housing of the head portion 36. In such instances, the housing may define an aperture 80 opposite the flow control device 39 from the outlet end 42 of the tubular body 32, with the aperture 80 being in fluid communication with the cavity 52 so as to permit egress of aqueous humor through the flow control device 39 and the aperture 80, to the external location. In accordance with the disclosure herein, as shown in FIG. 6C, a filter 40 may be disposed subsequent to (i.e., downstream) of the flow control device 39, opposite to the outlet (proximal) end 42 of the tubular body 32 from the flow control device 39. For example, the filter 40 may be engaged with the aperture 80 about the outlet of the head portion 36. In such aspects, the filter 40 may be configured to filter contaminants from any backflow to the flow control device 39, to preclude external contaminants from reaching the flow control device 39, or such that the filter 40 cooperates with the flow control device 39 to resist or prevent bacterial incursion into the tubular body 32 leading to the interior of the eye.

In one aspect, at least the portion of the flow control device 39 defining the conduit 38 may be configured to dilate in response to the intraocular pressure being above a preselected pressure (see, e.g., FIGS. 11A-11C, and 12A-12B). Such dilation or expansion of the cross-sectional area of the conduit 38 allows a flow, or an increase in the flow, or a decrease in the resistance to the flow, of the aqueous humor through the conduit 38 to the external location, thereby reducing and/or stabilizing the intraocular pressure to less than or equal to the preselected pressure. That is, at least the portion of the flow control device 39 defining the conduit 38 may be configured to have pressure-responsive dilation properties. In other instances, at least the portion of the flow control device 39 defining the conduit 38 may be configured to have an actuator (not shown) engaged therewith, with the actuator being configured to cause dilation of at least the portion of the flow control device 39 defining the conduit 38. In some aspects, at least the portion of the flow control device 39 defining the conduit 38 may be configured such that the conduit 38 is normally constricted to prevent flow of the aqueous humor therethrough (i.e., the conduit 38 is normally closed). Once dilated in response to the intraocular pressure exceeding the preselected pressure, the conduit 38 may also be configured to be constrictable or to constrict, in response to decreased aqueous humor production causing the intraocular pressure to fall below the preselected pressure, to decrease or halt the flow or to increase resistance to flow of the aqueous humor through the conduit 38 to the external location and thereby allowing the intraocular pressure to increase to no greater than the preselected pressure. This pressure-responsive dilation property of the portion of the flow control device 39 defining the conduit 38 may thus be operable to regulate the flow of the aqueous humor and thus not only reduce the intraocular pressure into accordance with the preselected pressure, but also facilitate stabilization of the intraocular pressure regardless of the particular patient's aqueous humor dynamic properties (i.e., individual rate of production of the aqueous humor depending on the day or time of day).

Figure 15A:
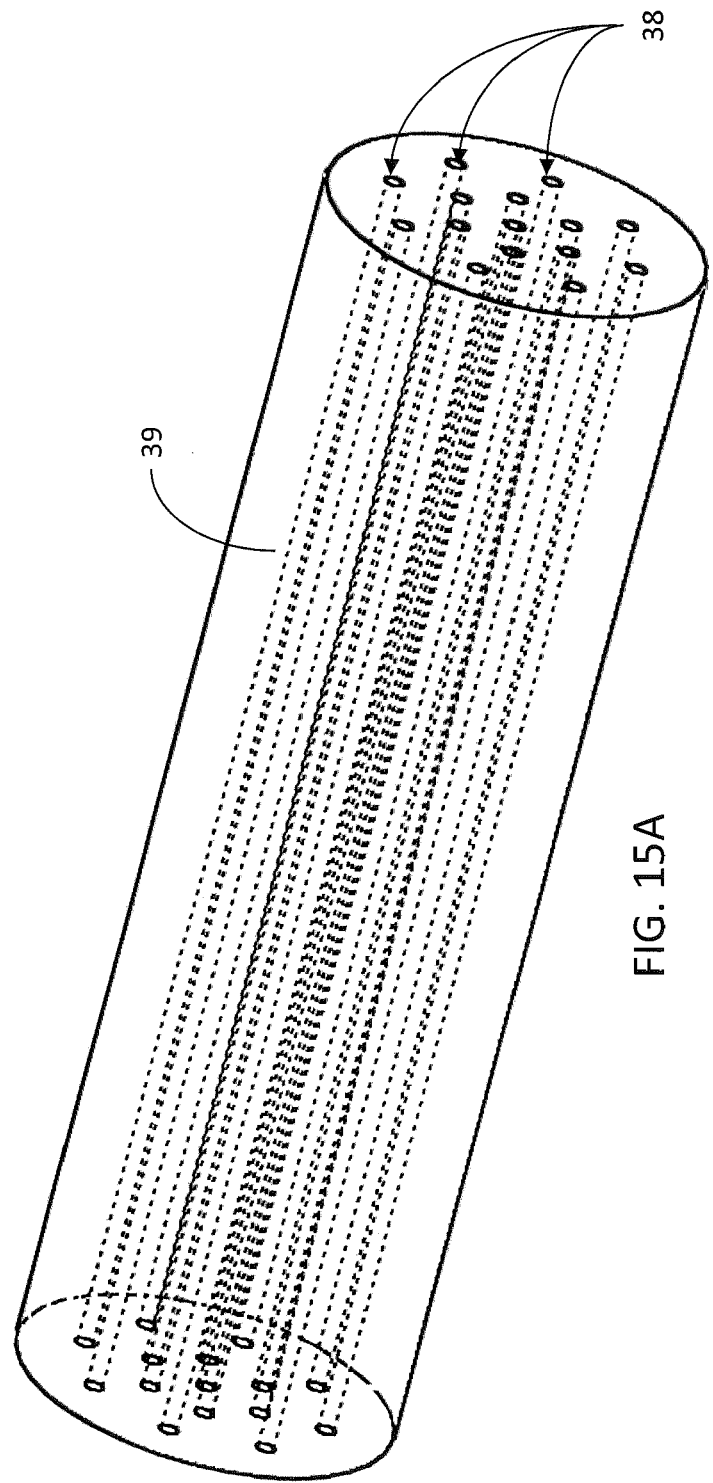
Figure 15B:
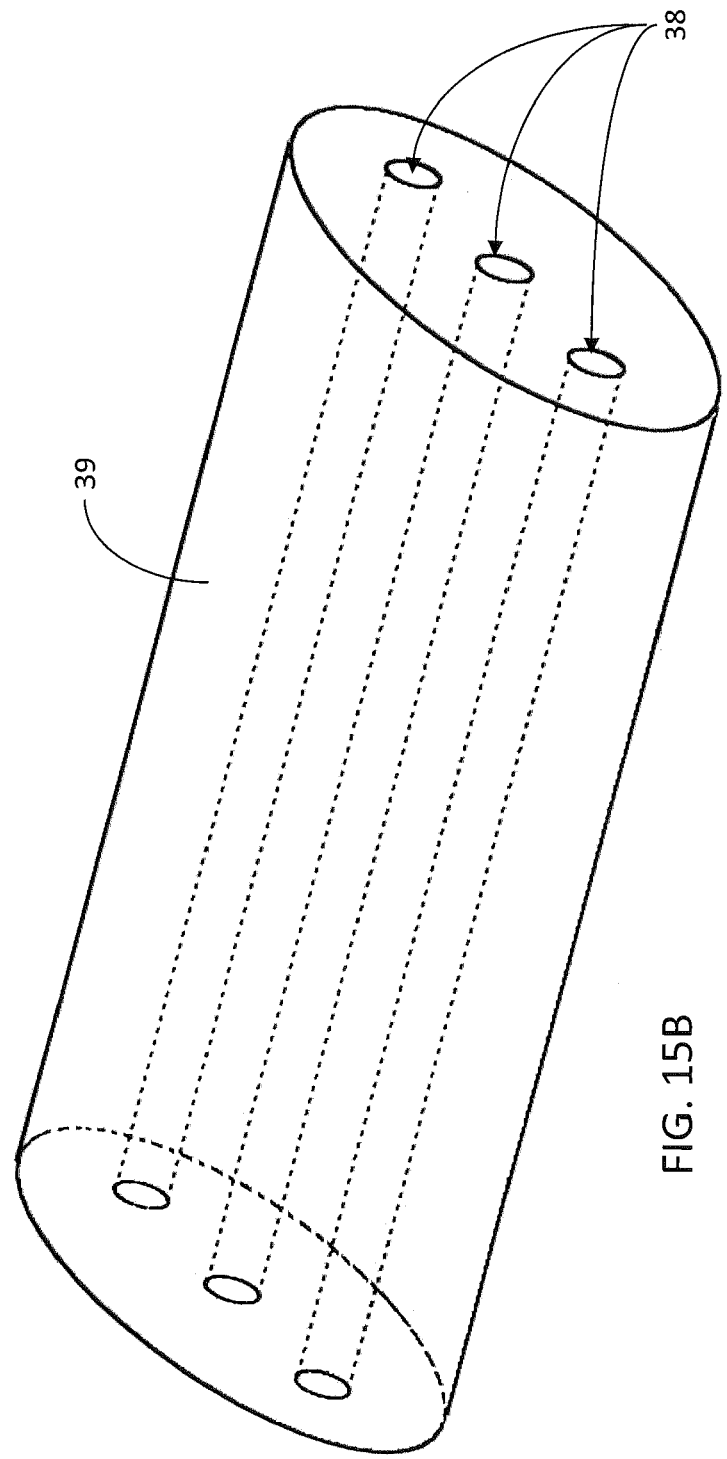
Figure 16A:
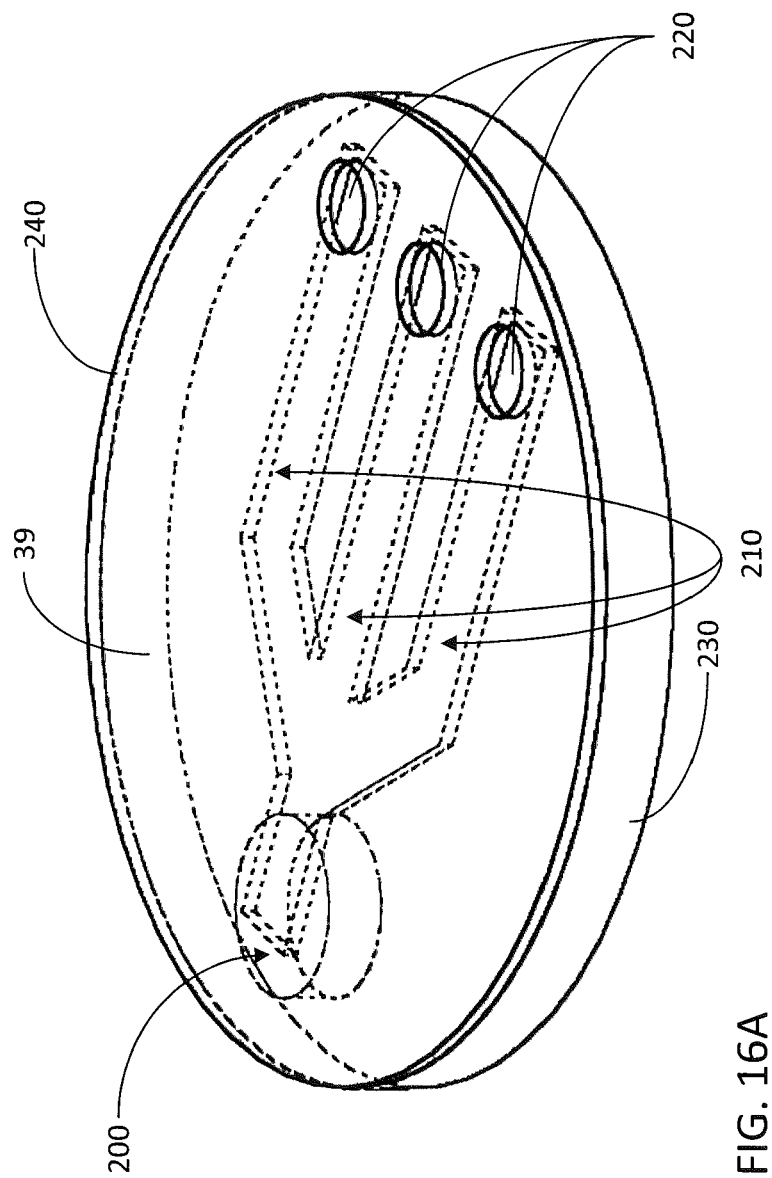

In some aspects, the flow control device 39 may be configured to define a plurality of conduits 38 in communication between the cavity 52 and the external location (see, e.g., FIGS. 15A and 15B). In such instances, at least one of the conduits 38 is dilatable, for example, in response to intraocular pressure exceeding a preselected pressure or upon actuation of the dilation by an appropriate actuator (not shown). The plurality of conduits 38 may be arranged in parallel and in communication between the cavity 52 and the external location. As shown in FIG. 16A, the conduit 38 may comprise, for instance, a single inlet port 200 in fluid communication with the cavity 52 defined by the housing, and a plurality of outlet ports 220 each in fluid communication with the inlet port 200 through respective channels 210 extending from the inlet port 200. In another configuration, as shown in FIG. 16B, the channels 210 may be configured to extend radially outward from the single inlet port 200 such that the outlet ports 220 are angularly spaced apart about the inlet port 200.

In another aspect, as shown in FIG. 13, the flow control device 39 may include a first portion 230 defining a single inlet port 200 in fluid communication with the cavity 52 defined by the housing of the head portion 36, and a second portion 240 defining a plurality of outlet ports 220. In such an aspect, the first and second portions 230, 240 are configured to be complementarily engaged so as to define a reservoir 250 therebetween, wherein the outlet ports 220 are each in fluid communication with the inlet port 200 via the reservoir 250. Since the second portion 240 defines the outlet ports 220, and may thus be directed outwardly of the head portion 36, the second portion 240 may be configured to be relatively rigid so as to resist deformation in response to a force applied thereto. In particular instances, the first and second portions 230, 240 may be configured to be responsive, for example, to an output of a laser device (not shown) so as to attach the components together.

In each aspect disclosed herein, the housing of the head portion 36 may be configured such that the flow control device 39 operably engaged therewith is removable or replaceable with respect to the housing. That is, the flow control device 39 may be removable/replaceable with respect to the housing, whether disposed within the cavity 52, or engaged with the aperture 80 defined by the housing. Further, the flow control device 39 maybe removable/replaceable with respect to the housing, whether or not a filter 40 is disposed subsequently to/downstream of the flow control device 39. In addition, the flow control device 39 may be removable/replaceable with respect to the housing, in order that a filter 40 disposed upstream of the flow control device 39 (i.e., in engagement with the outlet end 42 of the tubular body 32) may also be removable/replaceable.

Figure 9:
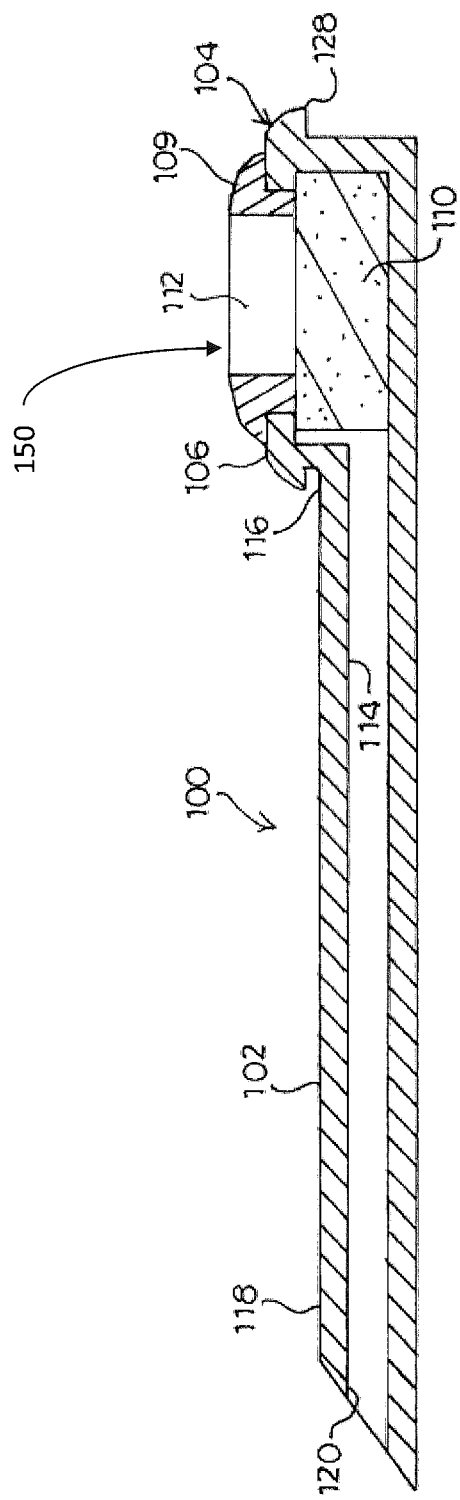
FIG. 9 is a longitudinal cross-section elevation view of the drainage device as shown in FIG. 7.
Figure 10:
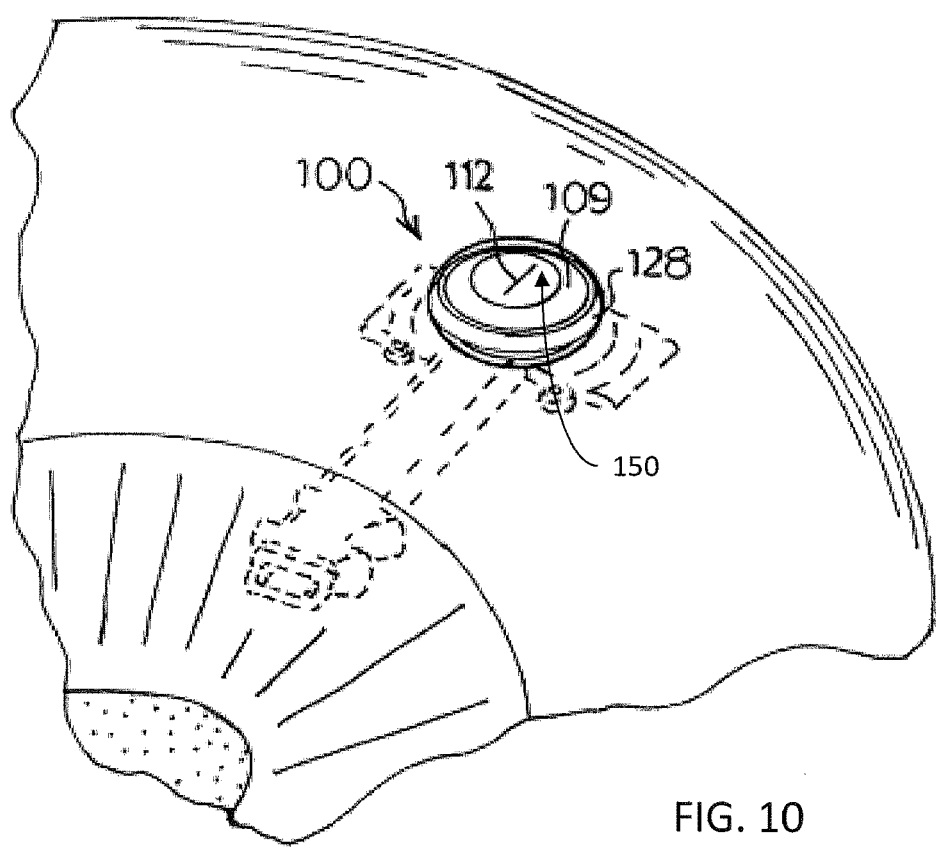
FIG. 10 is a perspective schematic view of the drainage device as shown in FIG. 7 implanted in an eye.
Figure 11A:
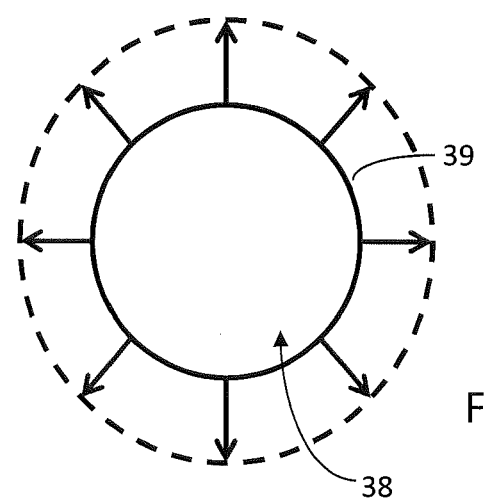
FIGS. 11A-11C schematically illustrate dilation configurations of a conduit defined by a flow control device associated with a drainage device, perpendicularly to the direction of flow of a fluid therethrough, according to one embodiment of the present disclosure.
Figure 11B:
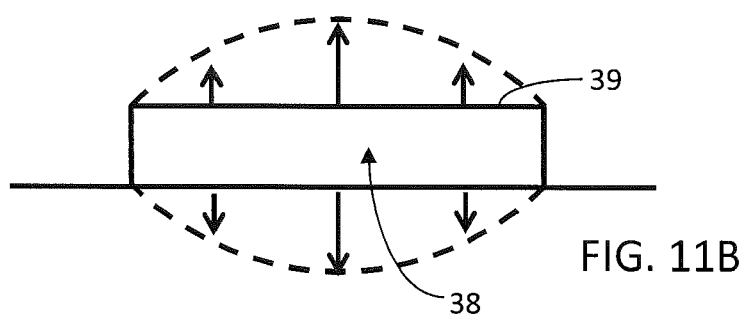
Figure 11C:
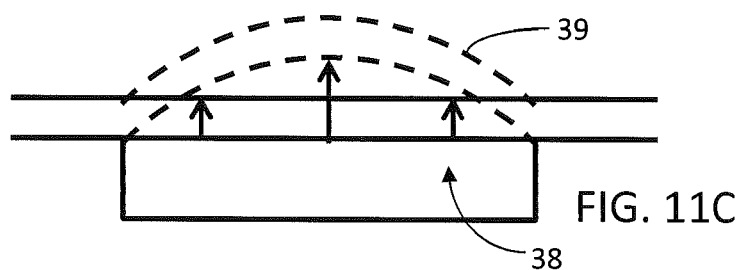
Figure 12A:
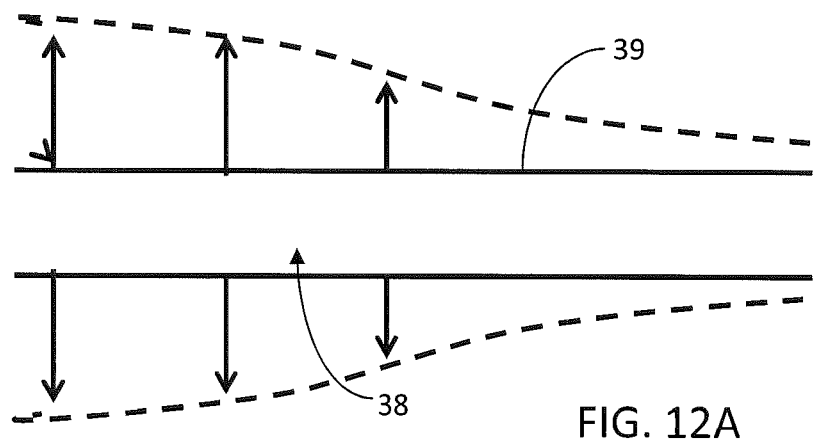
FIGS. 12A and 12B schematically illustrate dilation configurations of a conduit defined by a flow control device associated with a drainage device, parallel to the direction of flow of a fluid therethrough, according to one embodiment of the present disclosure.
Figure 12B:
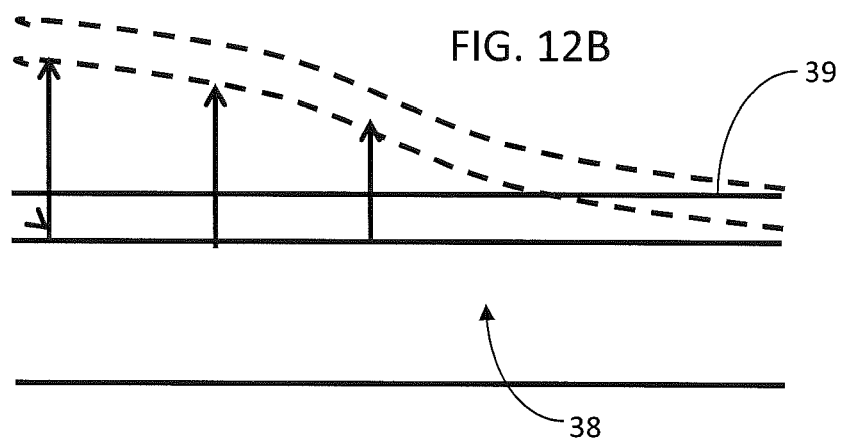
Figure 14:
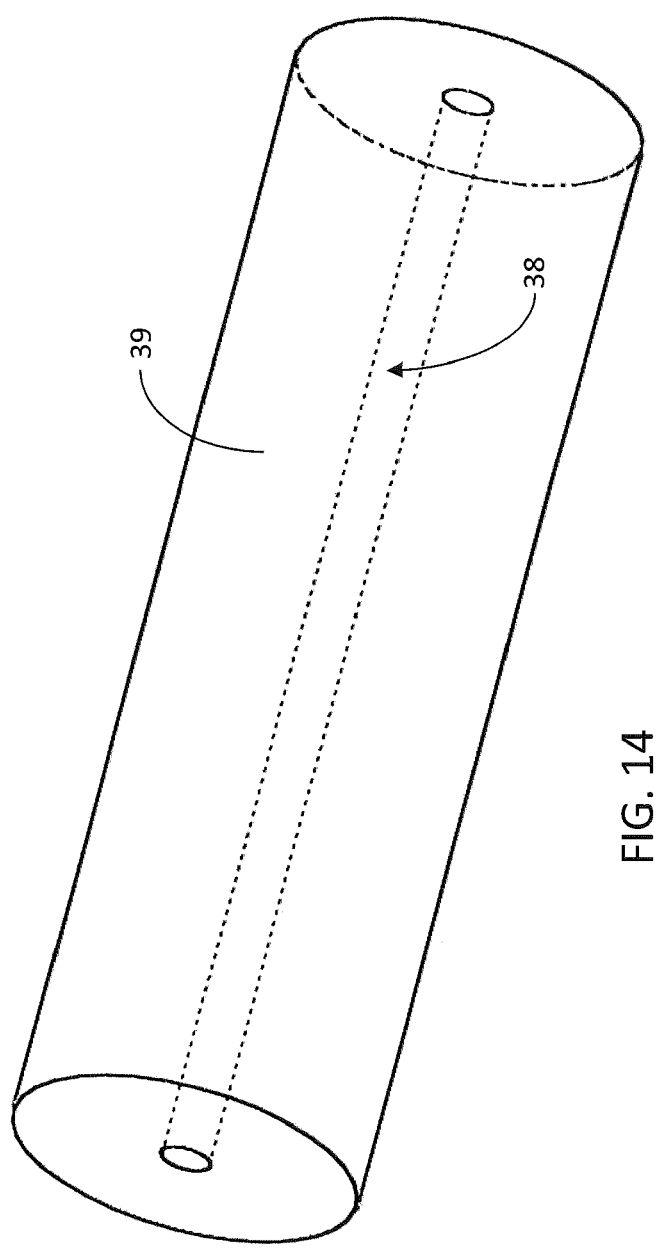
FIGS. 14, 15A, and 15B schematically illustrate configurations of flow control device for a drainage device, according to various embodiments of the present disclosure.

For example, as shown in FIGS. 7-10, and generally designated at 100, the drainage device 100 may comprise a tubular body 102 and an outlet assembly 104, wherein the outlet assembly 104 includes a head portion 106 defining an opening 108 configured for insertion and removal of a filter 110 into the head portion 106. A removable circular cap 109 having a flow control device 150 engaged therewith, is provided for sealing the opening 108 and for accessing the interior of the head portion 106 via a conduit (shown, for example, as slit 112, though any of the flow control device configurations disclosed herein having a dilatable conduit may be applied). At least a portion of the tubular body 102 of the drainage device 100 is implantable into the anterior chamber of an eye for draining aqueous humor therefrom. The tubular body 102 of the drainage device 100 may be substantially ovular and defines a lumen 114 that extends between a proximal end 116 and the distal end 118 of the tubular body 102. The distal end 118 of the tubular body 102 defines at least one opening 120 communicating with the lumen 114 and functioning as a fluid inlet. One or more tapered projections 122, or barbs, may be provided adjacent the distal end 118 of the tubular body 102. The head portion 106 of the outlet assembly 104 may further comprise integral radial tabs 124 extending outwardly from a longitudinal axis of the drainage device 100. FIG. 9 illustrates that the head portion 106 may define an interior cavity 126 in fluid communication with the lumen 114 of the tubular body 102, wherein the interior cavity 126 is configured to accommodate and receive the filter 110. A circular rim 128 extends radially outward of the surface of the head portion 106 for defining the opening 120. The filter 110 is disposed within the head portion 106 and is configured such that the outlet of the lumenal passage of the tubular body 102 is closed or substantially closed or otherwise occupied by the filter 110. The filter 110 is configured to prevent bacterial migration toward the interior of the eye, and may be configured to regulate or facilitate regulation of intraocular pressure by providing a predetermined resistance to outflow of aqueous humor from the anterior chamber of the eye toward the external location (i.e., the tear film). The flow control device 150 in the cap 109 may be configured to permit the outflow of aqueous humor that has passed through the filter 110 to flow outward to the external location (i.e., onto the sclera and to enter the tear film), while providing resistance to aqueous humor outflow and restriction against backflow or bacterial incursion.

The flow control device 39, or at least the portion thereof defining the conduit 38, may be comprised of a flexible bio compatible material such as, for example, polyurethane or silicone. In some instances, the flow control device 39, or the material from which the flow control device 39 is comprised, may be configured to be responsive, for example, to an output of a laser device (not shown) so as to form or open additional dilatable channels therein or to attach components together. That is, a laser light output directed at the material comprising the flow control device 39 may cause the formation or opening of additional conduits 38, as necessary or desired for controlling the flow of aqueous humor from the eye, and thus controlling the intraocular pressure. In particular instances, the flow control device 39, or the material from which the flow control device 39 is comprised, may also be configured to be responsive, for instance, to the output of the laser device to seal or constrict a conduit 38 defined thereby. That is, one or more of the conduits 38 can be sealed or constricted, as necessary or desired, to control the flow or manipulate the resistance to flow of aqueous humor from the eye. In particular aspects, the laser modification of the conduits defined by the flow control device 39, or the material from which the flow control device 39 is comprised, may be accomplished in situ, with the drainage device 30 in place with respect to the eye. The flow control device 39 may be fabricated by any suitable microfabrication technique or process, in addition or in the alternative to the responsiveness thereof to the output of a laser device. For example, photolithography/deposition techniques, casting, molding, or any other suitable technique or combinations thereof may be implemented for forming the flow control device 39.

As shown in FIG. 11, the flow control device 39, or at least the conduit(s), channel(s), and port(s) associated therewith, may be configured to open (dilate) and close (constrict) to regulate and/or stabilize the flow of the aqueous humor from the interior cavity 52 of the head portion 36 to the external location (i.e., to flow onto the sclera and enter the tear film) and, in doing so, maintains the intraocular pressure within a normal range of about 7 mmHg to about 20 mmHg. For example, when the intraocular pressure exceeds a preselected pressure, the conduit 38 will dilate, or is actuated to dilate, and permit the aqueous humor to exit the outlet assembly 34 (i.e., by reducing or decreasing the resistance to flow of the aqueous humor). When the intraocular pressure is reduced below the preselected pressure, due to the flow of the aqueous humor through and from the outlet assembly 34, the conduit 38 will constrict to its normal state (closed or partially open) and limit, or inhibit, the aqueous humor from exiting the head portion 36 (i.e., increase the resistance to flow of the aqueous humor). The conduit 38 will remain in its normal state (closed or partially open) until the intraocular pressure again reaches or exceeds the preselected pressure, at which time the conduit 38 will re-dilate to permit, or enhance, further drainage or reduced resistance to flow of the aqueous humor. In some aspects, the portion of the flow control device 39 defining the conduit 38 may be configured to be dilatable in the direction of flow of the aqueous humor, or perpendicularly to the direction of flow of the aqueous humor. One skilled in the art will appreciate that, due to the overall size of the drainage device 30 for the applications disclosed herein, the conduit(s), channel(s), and port(s) associated with the flow control device 39 are formed with micro-scale or nano-scale relative dimensions, and the manufacturing techniques and processes implemented in the production thereof are therefore selected accordingly.

Accordingly, the drainage device 30 provides drainage of the anterior chamber of the eye through the drainage device 30, based on the intraocular pressure, and reduces the likelihood for over-draining the anterior chamber and causing hypotony. Additionally, the flow control device 39, with essentially a one-way (anti-backflow) valve structure, prevents backflow of the aqueous humor. One skilled in the art will therefore appreciate that any suitable type and arrangement of a pressure-actuated check valve may be implemented consistently with the application parameters disclosed herein.

In addition to the materials already described, at least the tubular body and the outlet assembly of the embodiments of drainage device 30, 100 may be formed from materials having good biocompatibility and durability, and which are sufficiently flexible. Suitable materials include a material selected from the group consisting of silicone, acrylic, polyimide, polypropylene, polymethyl methacrylate, polytetrafluoroethylene, hydrogels, polyolefin, polyolefin resins such as polyethylene, polyisobutylene, ethylene-vinyl acetate copolymer, polynorbornene, polyvinylchloride, polyester, polyvinyl alcohol, polyvinyl pyrolidone, polyethersulfone (PES), poly(styrene-isobutyl-styrene), polysilicon, polyurethane, polycarbonate urethane, glass and ceramics such as alumina and titania, metals such as stainless steel, titanium, gold, silver, platinum or nitinol, collagen or chemically-treated collagen, hydroxyapetite, natural and synthetic rubbers such as polybutadiene, polyisoprene, SBR (Styrene Butadiene Rubber), and SIR, polyacetal resin, ABS (Acrylonitrile-Butadiene-Styrene) resin, solid HEMA polymer, and combinations thereof.

At least a portion of the filter(s) 40 has a pore size that is sufficiently small to prevent ingress or backflow of microorganisms, such as bacteria, viruses, fungi and spores thereof, from entering the lumen 46, so as to minimize the opportunity for reflux infection in the eye. A pore size of less than about 0.4 µm is sufficiently small to prevent ingress or backflow of microorganisms. In some embodiments, the filter 40 may comprise a microporous/nanoporous membrane or polymer network, fiber network, or microcapsular material having a network of pores. Microporous filter membranes suitable for use with ophthalmic devices include micropore filter membranes (polycarbonate, polyethersulfone, polyvinylidene fluoride, polytetrafluoroethylene), porous hydrogels (polyacrylamide, alginate, polyhydroxyethylmethacrylate), and microperforated silicone or polyvinyl polymer, such as polyvinyl alcohol, which is expandable within the lumen 46. Other suitable polymers include a polyolefin polymer, an ethylene-vinyl alcohol copolymer, a polyacrylonitrile polymer, a cellulose polymer, cellulose acetate polymer, and a polyamide polymer. Filter membrane nanotechnology may also be useful to fabricate microporous membranes to be biocompatible, non-degradable, and immune-isolating. Other materials, such as ceramics, polymers and metals, such as titanium, may also be suitable for the filter. The filters may be created using lithography or electrospinning. In some instances, the filter 40, 110 may have an antibiotic coating to prevent contamination during replacement. Suitable coatings for the filter are described in co-pending U.S. Patent Application Publication No. 2010/0057055, the contents of which are hereby incorporated by reference in their entirety.

At least a portion of the external surfaces of the body, the tabs, and/or the inner surface of the head portion of the drainage device 30, 100 may be coated with a porous cellular ingrowth coating. The porous cellular ingrowth coating is coated on at least the portion of the drainage device 30, 100 that is in contact with the sclera and conjunctiva when the drainage device is implanted. The porous cellular ingrowth coating may be a hydroxyapatite or porous polyethylene, which serves to promote cell adhesion. Selected growth factors may be adsorbed such that the body and the tabs of the drainage device 30, 100 may be securely anchored in position. This enables the drainage device 30, 100 to resist in situ motion and displacement. To further promote tissue ingrowth and cell attachment, the body of the drainage device 30, 100 may include surface alterations, such as texturing, roughening or other patterned or non-patterned irregularities.

The remaining surfaces of the drainage device 30, 100, including the entire lumenal surface, the portions of the external surface of the drainage device not in contact with the sclera, and/or the filter surfaces, may be coated with a bio-inert surface coating to enhance surface biocompatibility. Such coatings may include bio-inert polymer coatings such as phosphoryl choline (PC), polyethylene glycol (PEG), sulfobetaine (SB), carboxybetaine (CB), and polyethylene oxide (PEO). These polymer coatings down-regulate deleterious biological reactions, primarily by attracting a large and stable hydration shell when grafted onto a surface. Bio-inert surface coatings may be further modified with biologically active molecules such as heparin, spermine, surfactants, proteases or other enzymes, or other biocompatible chemicals amendable to surface immobilization. PEO also is amenable to end-group coupling for surface immobilization of the biologically active molecules. The addition of such bioactive molecules could advantageously impart specific desired functionality, for example, allowing a further increase in the hydrophilicity of the surface.

The coating for the drainage device 30, 100 can also comprise material that includes a therapeutic agent, as well as antifibrotic and/or antimicrobial and/or anti-fouling agents. The therapeutic agent can be selected from the group consisting of heparin, selenium, TGF-beta, an intraocular pressure-lowering drug, and an anti-proliferative agent. The coatings can be, for example, a drug eluting coating, an antithrombogenic coating, and/or a lubricious coating. Materials that may be used for a drug-eluting coating include parylene C, poly(butyl methacrylate), poly(methyl methacrylate), polyethylene-co-vinyl acetate, and other materials known in the art. Anti-microbial coatings may include, for example selenium, silver, melimine, or fimbrolides or other quorum sensing inhibitors. In addition, these agents may be incorporated into the filter material or other components of the drainage device 30, 100 via covalent, metallic, ionic, or non-covalent bonding, or by surface adsorption.

Figure 17:
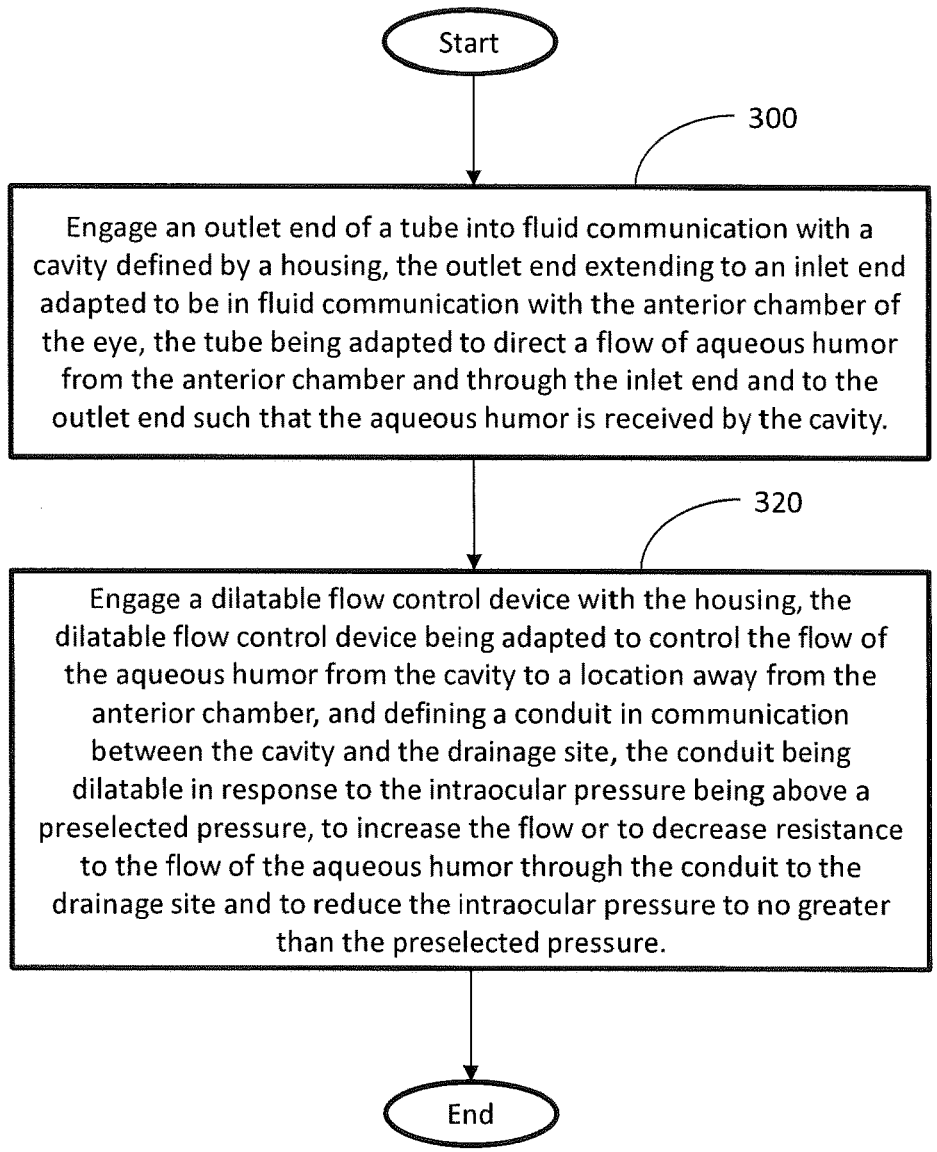
FIG. 17 schematically illustrates a method of manufacturing a drainage device, according to one aspect of the present disclosure.

Another aspect of the disclosure herein is directed to a method of manufacturing an apparatus for draining aqueous humor from an eye for reducing and/or stabilizing intraocular pressure, as shown, for example, in FIG. 17. Such a method comprises engaging an outlet end of a tube into fluid communication with a cavity defined by a housing, wherein the outlet end extends to an inlet end adapted to be in fluid communication with the anterior chamber of the eye, and wherein the tube is adapted to direct a flow of aqueous humor from the anterior chamber and through the inlet end and to the outlet end such that the aqueous humor is received by the cavity (block 300). As shown in block 320, a dilatable flow control device is engaged with the housing, wherein the dilatable flow control device is adapted to control the flow of the aqueous humor from the cavity to a location external to the anterior chamber, and wherein the dilatable flow control device further defines a conduit in communication between the cavity and the external location. The conduit is dilatable in response to the intraocular pressure being above a preselected pressure, to increase the flow or decrease resistance to flow of the aqueous humor through the conduit to the external location and to reduce the intraocular pressure to no greater than the preselected pressure. Such a method of manufacture may be realized in conjunction with the drainage device(s) and components thereof as disclosed herein.

In relation to such a method of manufacture, a filter device may be engaged into fluid communication between the inlet end of the tube and the flow control device, for filtering contaminants from the aqueous humor prior to the flow control device. In some instances, the filter device may be engaged with the housing subsequent to the outlet end of the tube, such that the flow control device is removable or replaceable with respect to the housing, so as to allow the filter device to be removed or replaced. In another aspect, a filter device may be engaged into fluid communication with the flow control device, opposite to the outlet end of the tube from the flow control device, for filtering contaminants from any backflow to the flow control device and, in some instances, the filter device may be engaged with the housing subsequent to the flow control device, such that the filter device engaged therewith is removable or replaceable with respect to the housing. In yet another aspect, the dilatable flow control device may be inserted into the cavity defined by the housing. As disclosed herein with respect to aspects of the flow control device, at least the portion of the flow control device defining the conduit(s) may be comprised of a material that is responsive to the output of a laser device. As such, aspects of the method may include engaging the flow control device with an output of a laser device so as to form additional dilatable conduits in the flow control device, or to seal a conduit defined by the flow control device.

All aspects of the drainage device 30, 100 disclosed herein may be surgically implanted under topical anesthesia, possibly supplemented subconjunctivally. In general, the drainage device 30, 100 may be inserted into the sclera using routine operative procedures.

Figure 4:
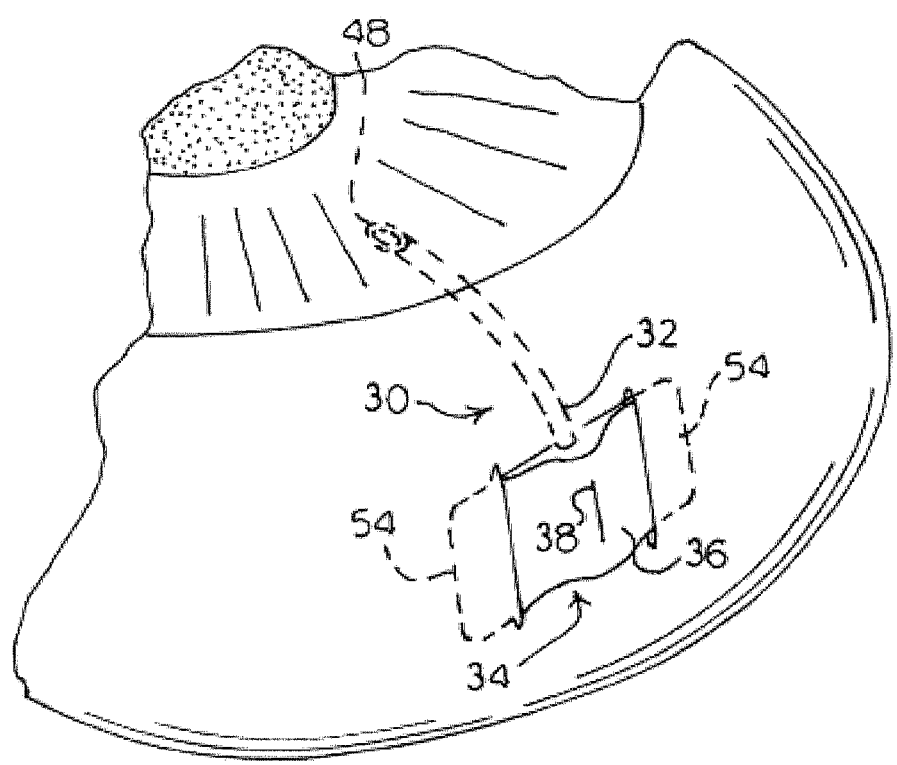
FIG. 4 is a perspective schematic view of the drainage device as shown in FIG. 1 implanted in an eye.
Figure 5:
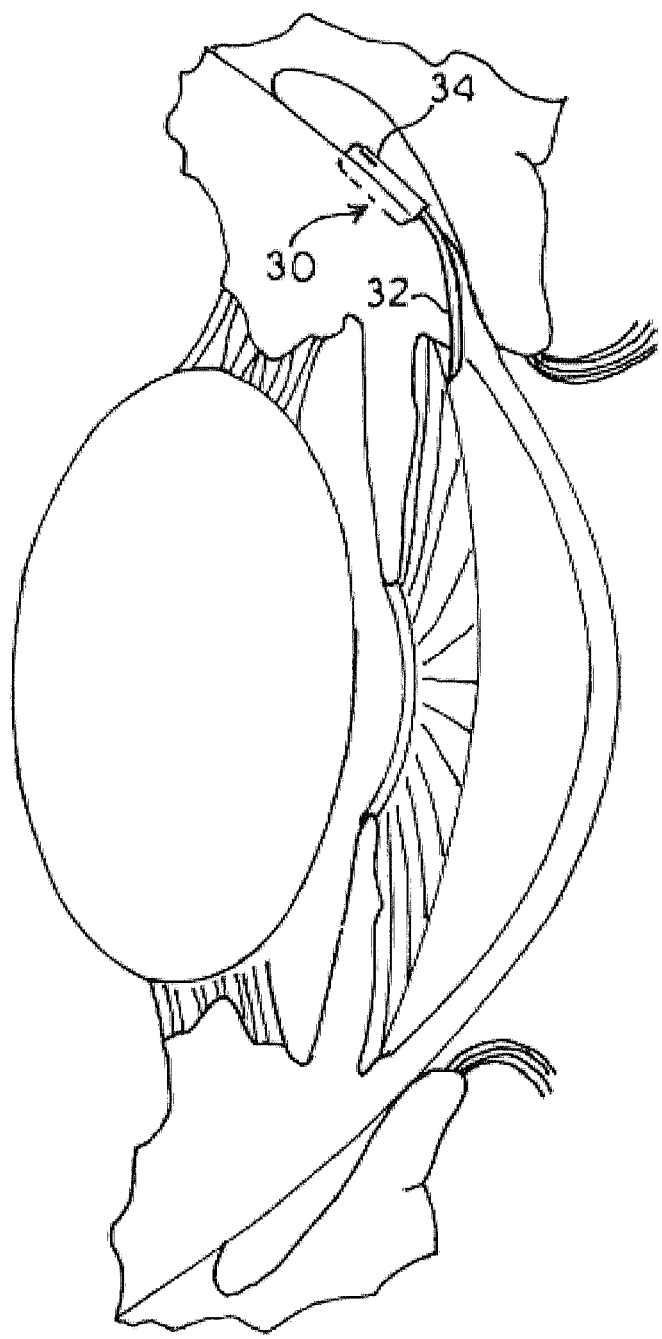
FIG. 5 is a side elevation view of the drainage device implanted in an eye as shown in FIG. 4.

As shown, for example, FIGS. 4 and 5 with respect to the one aspect of the drainage device 30, the procedure for implanting the drainage device 30 includes the initial step of dissecting or piercing the conjunctiva into Tenon's space about 4 mm from the limbus in the fornix space. The distal end 44 of the tube 32 is then threaded through the incision in the fornix so that the tubular body 32 passes under the conjunctiva and the outlet assembly 34 lies externally on the conjunctiva in the cul-de-sac region underneath the eyelid. The conjunctiva is then dissected down from the fornix incision to the limbus to expose the underlying sclera for insertion of the distal end 44 of the tube 32. A needle, trocar, scalpel, or any of a multitude of instruments familiar to ophthalmologic practitioners may be used at the site of the now exposed sclera to make a stab incision through the sclera into the anterior chamber. The pointed tip at the distal end 44 of the tubular body 32 is then inserted through the scleral tract of the incision and into the anterior chamber or posterior chamber of the eye. The remainder of the tubular body 32 remains positioned external to the ocular surface of the eye. Optionally, the tubular body 32 may be sutured to the sclera.

Next, two parallel cuts are made into the conjunctiva adjacent the outlet assembly 34 approximately 2 mm to 4 mm apart. A tab 54 is inserted into each cut. The tabs 54 may be sutured to the sclera with a 10-0 nylon suture. A suture is then used to close the conjunctiva around the tabs 54 while leaving the intermediate portion of the outlet assembly 34 exposed. In some embodiments, holes may be provided in the tabs for additional sutures into the sclera, providing further stability to the drainage device 30 until the biointegration is complete. Similarly, for aspects of the drainage device including suture bars, the suture bars are sutured into the sclera for securing the body of the device. The conjunctiva is then restored and the incision is closed with a suture using a known method or a biologically acceptable adhesive. For a drainage device 100 with lips or rims or a conduit, a purse-string 8-0 suture may be used to close the conjunctiva tightly around the outlet.

In use, aqueous humor flows into the drainage device 30 from the anterior chamber or posterior chamber of the eye and passes through the tubular body 32 via the lumen 46 and through the filter 40 and drains via the flow control device 39 in the outlet assembly 34. As disclosed, the flow path through the drainage device 30 can be configured for regulating drainage of aqueous humor at a predetermined rate (i.e., as regulated by the flow-through dimensions of the flow control device) so as to regulate the intraocular pressure at or below a predetermined or preselected pressure (i.e., a threshold), and further for resisting the incursion or backflow of microorganisms to the eye. The outflow of aqueous humor is consistently regulated at a preselected pressure by the filter 40 and flow control device 39, either separately or in combination, so that a predictable outflow rate or pressure response can be calculated for proper drainage for maintaining intraocular pressure at preselected pressure, generally between about 6 mmHg to about 18 mmHg and, more particularly, between about 8 mmHg and about 12 mmHg. The flow rate will range based on aqueous humor production, which is usually between about 1 µL/min and about 4 µL/min, while avoiding hypotony, which may occur at less than about 5 mmHg.

Figure 18:
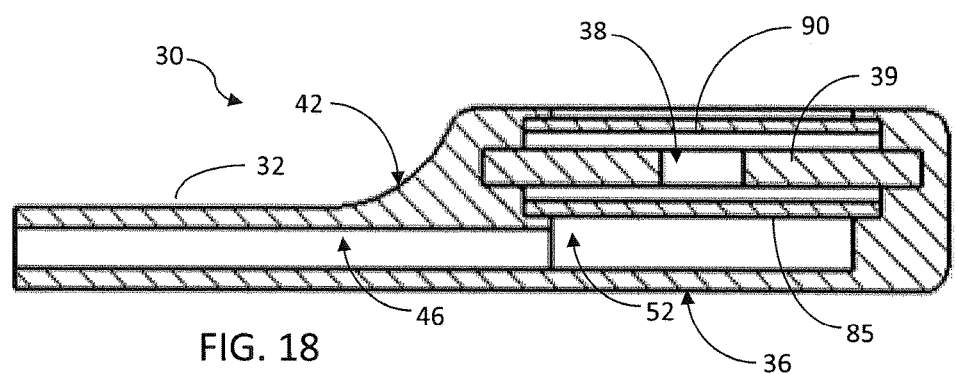
FIG. 18 schematically illustrates a dual filter configuration of a drainage device, according to one embodiment of the present disclosure.

In accordance with a further aspect of the disclosure herein (see, e.g., FIG. 18), an apparatus for draining aqueous humor from an eye for reducing and/or stabilizing intraocular pressure may also be provided, wherein such an apparatus 30 comprises a tube 32 extending between an inlet end and an outlet end 42, with the inlet end being adapted to be in fluid communication with the anterior chamber of the eye, and with the tube 32 being adapted to direct a flow of aqueous humor from the anterior chamber and through the inlet end to the outlet end 42. A flow control device 39 is operably engaged with the outlet end 42 and is configured to control a flow of the aqueous humor from the tube 32 to a location external to the anterior chamber, wherein the flow control device 39 defines a conduit 38 in communication between the outlet end 42 and the external location, and wherein the conduit 38 is dilatable in response to the intraocular pressure being above a preselected pressure, to increase the flow or to decrease resistance to flow of the aqueous humor through the conduit 38 to the external location and to reduce the intraocular pressure to no greater than the preselected pressure. In such an aspect, a first filter device 85 is disposed in fluid communication between the inlet end of the tube and the flow control device 39, wherein the first filter device is configured to filter contaminants from the aqueous humor prior to the flow control device 39, and a second filter device 90 is disposed in fluid communication with the flow control device 39, opposite to the outlet end 42 of the tube 32 from the flow control device 39, wherein the second filter device 90 is configured to filter contaminants from any backflow to the flow control device 39.

In some instances, the first filter device 85 is engaged with the outlet end 42 of the tube 32, and is operably engaged with the flow control device 39, such that the flow control device 39 is removable or replaceable with respect thereto, so as to allow the first filter device 85 to be removed or replaced. The second filter device 90 may be engaged with the flow control device 39 opposite to the first filter device 85, wherein the flow control device 39 is configured such that the second filter device 90 is removable or replaceable with respect thereto, so as to allow the second filter device 90 to be removed or replaced. In other instances, a housing defining a cavity may be in fluid communication with the outlet end of the tube, wherein the cavity is configured to receive the aqueous humor, and wherein the housing is configured to operably engage the flow control device such that the flow control device regulates the flow of the aqueous humor from the cavity. The "dual filter" configuration incorporates components of the drainage device(s) as otherwise disclosed herein, particularly wherein a filter 85, 90 is disposed both upstream and downstream of the flow control device 39. The dual filter configuration thus, for example, provides for filtering of the aqueous humor and preventing backflow of contaminants in regard to the drainage device, and removes the requirements regarding clogging resistance or contaminant migration from the flow control device 39 itself. In some aspects, each of the first and second filters 85, 90 and the flow control device 39 may be configured to be individually removable and replaceable. However, different combinations of the first and second filters and the flow control device may be configured to be removable and replaceable, including all three components as a single unit.

The dual filter configuration having the flow control device disposed therebetween may provide a physiologic design to control and/or stabilize pressure in the eye. The flow control device is implemented as an episcleral venous pressure device to provide a preselected lower pressure limit of the intraocular pressure. The filters may provide resistance in the manner of the trabecular meshwork in a human eye. The combination may thus provide a natural pressure change in the eye based on diurnal changes in aqueous humor production and ocular pulse. Thus, the aspects of the drainage device 30, 100 described herein effectively provide outflow characteristics which model and account for the aqueous humor dynamics of a healthy eye which may vary from person to person. The aspects of the drainage device 30, 100 disclosed herein may comprise any of the materials previously disclosed. The drainage device 30, 100 can be fabricated through conventional micro machining techniques or through procedures commonly used for fabricating optical fibers or semiconductors or other micro-scale or nano-scale systems. For example, in some embodiments, the drainage devices 30, 100 are drawn with a bore, or lumen, extending therethrough. In some embodiments, the tapered tip at the distal end of the body can be constructed by shearing off an end of the tubular body. This can create the tapered portion that can be used to puncture or incise the eye tissue during implantation and dilate the puncture or incision during advancement of the drainage device 30, 100. Other methods of manufacturing the drainage device 30 can be implemented, as will be appreciated by one skilled in the art.

Each of the aspects of the drainage device 30, 100 provides a method for treating glaucoma wherein the aqueous humor is permitted to flow out of an anterior chamber or posterior chamber of the eye through a surgically implanted pathway to a location external to the anterior or posterior chamber. The drainage device 30, 100 is implanted with minimal invasiveness of the ocular tissue and minimal sense of a foreign object to the person in which it is implanted. Immobilizing the outlet assembly of the drainage device 30, 100 is an important feature. Immobilization is enhanced by using a biocompatible material and by providing the portions of the drainage device 30, 100 with the porous cellular ingrowth surface in contact with eye tissue to promote tissue integration to the sclera. Coating the surface of the drainage device 30, 100 with polymers or biologically active molecules, or providing active agents within the polymers, also promotes surface biocompatibility or immobilization, post-implantation. All of these features contribute to minimizing problems caused by eye movement (micromotion), including a feeling of invasiveness to the ocular tissues, pain, and displacement of the drainage device 30, 100. Eliminating micromotion may also prevent adverse events such as fibrosis, erosion, exposure, and/or extrusion.

In addition, the embodiments of the drainage device 30, 100 as disclosed herein can be used to treat other ocular disorders, in addition to glaucoma. In one example, the drainage device 30, 100 may be used to treat dry eye, wherein the aqueous humor exiting the drainage device combines with the tear film for enhancing moisture and lubrication in the eye.

Many modifications and other aspects of the disclosure will come to mind to one skilled in the art to which this disclosure pertains having the benefit of the teachings presented in the foregoing descriptions and the associated drawings. Therefore, it is to be understood that the disclosure is not to be limited to the specific aspects disclosed herein and that modifications and other aspects are intended to be included within the scope of the appended claims. Although specific terms are employed herein, they are used in a generic and descriptive sense only and not for purposes of limitation.

That which is claimed:

1. An apparatus for draining aqueous humor from an eye for reducing or stabilizing intraocular pressure, the eye having an anterior chamber and including a cornea, a surrounding marginal limbus by which the cornea is continuous with a scleral layer and a conjunctival layer, and an external ocular surface of the eye under an eyelid, the apparatus comprising:

a tube extending between an inlet end and an outlet end, the inlet end being adapted to be in fluid communication with the anterior chamber of the eye, and the tube being adapted to direct a flow of aqueous humor from the anterior chamber and through the inlet end to the outlet end;

a housing defining a cavity in fluid communication with the outlet end of the tube, the cavity being configured to receive the aqueous humor; and a flow control device operably engaged with the housing and configured to control the flow of the aqueous humor from the cavity to a location external to the anterior chamber, the flow control device including at least one conduit extending between the cavity and the external location, the at least one conduit configured to allow the flow of the aqueous humor from the cavity to the external location, an elongate portion of the at least one conduit formed from a flexible material configured to provide varying flow resistance as the aqueous humor continues to flow through the at least one conduit from the cavity to the external location, the flexible material defining a transverse cross-sectional area for the elongate portion of the at least one conduit, wherein in response to each of various increases in the intraocular pressure, the flexible material is configured to expand to respectively increase the transverse cross-sectional area along the elongate portion of the at least one conduit, the flow resistance decreasing as the cross-sectional area increases, and in response to each of various decreases in the intraocular pressure, the flexible material is configured to contract to respectively decrease the transverse cross-sectional area along the elongate portion of the at least one conduit, the flow resistance increasing as the cross-sectional area decreases.

2. The apparatus of claim 1, comprising a filter device disposed in fluid communication between the inlet end of the tube and the flow control device, the filter device being configured to filter contaminants from the aqueous humor prior to the flow control device.

3. The apparatus of claim 2, wherein the filter device is engaged with the housing subsequent to the outlet end of the tube, and wherein the housing is configured such that the flow control device operably engaged therewith is removable or replaceable with respect to the housing, so as to allow the filter device to be removed or replaced.

4. The apparatus of claim 1, comprising a filter device disposed in fluid communication with the flow control device, opposite to the outlet end of the tube from the flow control device, the filter device being configured to filter contaminants from any backflow to the flow control device.

5. The apparatus of claim 4, wherein the filter device is engaged with the housing subsequent to the flow control device, and wherein the housing is configured such that the filter device engaged therewith is removable or replaceable with respect to the housing.

6. The apparatus of claim 1, wherein the flow control device includes at least one additional conduit extending between the cavity and the external location.

7. The apparatus of claim 6, wherein the conduits are arranged in parallel.

8. The apparatus of claim 1, wherein the at least one conduit comprises a single inlet port in fluid communication with the cavity defined by the housing, and a plurality of outlet ports each in fluid communication with the inlet port through respective channels extending from the inlet port.

9. The apparatus of claim 8, wherein the channels extend radially outward from the single inlet port such that the outlet ports are angularly spaced apart about the inlet port.

10. The apparatus of claim 1, wherein the flow control device includes a first portion defining a single inlet port in fluid communication with the cavity defined by the housing, and a second portion defining a plurality of outlet ports, the first and second portions being configured to be complementarily engaged so as to define a reservoir therebetween, with the outlet ports each being in fluid communication with the inlet port via the reservoir.

11. The apparatus of claim 10, wherein the second portion is rigid so as to resist deformation in response to a force applied thereto.

12. The apparatus of claim 1, wherein the flow control device is configured to be responsive to an output of a laser device so as to form at least one additional conduit therein.

13. The apparatus of claim 1, wherein the flow control device is configured to be responsive to an output of a laser device to seal the at least one conduit.

14. The apparatus of claim 1, wherein the housing is configured such that the flow control device operably engaged therewith is removable or replaceable with respect to the housing.

15. The apparatus of claim 1, wherein the flow control device is disposed within the cavity defined by the housing.

16. The apparatus of claim 15, wherein the housing defines an aperture opposite the flow control device from the outlet end of the tube, the aperture being in fluid communication with the cavity so as to permit egress of aqueous humor therethrough to the external location.

17. The apparatus of claim 1, further comprising an anchoring device operably engaged with the housing, the anchoring device being configured to engage the eye subconjunctivally so as to secure at least the housing to the eye.

18. The apparatus of claim 1, wherein the at least one conduit is configured to be normally constricted to prevent flow of the aqueous humor therethrough.

19. The article of claim 1, wherein the flow control device is comprised of a biocompatible material.

20. The article of claim 1, wherein the flexible material forming the at least one conduit includes of polyurethane or silicone.

21. A method of manufacturing an apparatus for draining aqueous humor from an eye for reducing or stabilizing intraocular pressure, the eye having an anterior chamber and including a cornea, a surrounding marginal limbus by which the cornea is continuous with a scleral layer and a conjunctival layer, and an external ocular surface of the eye under an eyelid, the method comprising:

engaging an outlet end of a tube into fluid communication with a cavity defined by a housing, the outlet end extending to an inlet end adapted to be in fluid communication with the anterior chamber of the eye, the tube being adapted to direct a flow of aqueous humor from the anterior chamber and through the inlet end and to the outlet end such that the aqueous humor is received by the cavity; and engaging a flow control device with the housing, the flow control device being adapted to control the flow of the aqueous humor from the cavity to a location external to the anterior chamber, and including at least one conduit extending between the cavity and the external location, the at least one conduit configured to allow the flow of the aqueous humor from the cavity to the external location, an elongate portion of the at least one conduit formed from a flexible material configured to provide varying flow resistance as the aqueous humor continues to flow through the at least one conduit from the cavity to the external location, the flexible material defining a transverse cross-sectional area for the elongate portion of the at least one conduit, wherein in response to each of various increases in the intraocular pressure, the flexible material is configured to expand to respectively increase the transverse cross-sectional area along the elongate portion of the at least one conduit, the flow resistance decreasing as the cross-sectional area increases, and in response to each of various decreases in the intraocular pressure, the flexible material is configured to contract to respectively decrease the transverse cross-sectional area along the elongate portion of the at least one conduit, the flow resistance increasing as the cross-sectional area decreases.

22. The method of claim 21, comprising disposing a filter device into fluid communication between the inlet end of the tube and the flow control device, for filtering contaminants from the aqueous humor prior to the flow control device.

23. The method of claim 22, comprising engaging the filter device with the housing subsequent to the outlet end of the tube, such that the flow control device is removable or replaceable with respect to the housing, so as to allow the filter device to be removed or replaced.

24. The method of claim 21, comprising engaging a filter device into fluid communication with the flow control device, opposite to the outlet end of the tube from the flow control device, for filtering contaminants from any backflow to the flow control device.

25. The method of claim 24, comprising engaging the filter device with the housing subsequent to the flow control device, such that the filter device engaged therewith is removable or replaceable with respect to the housing.

26. The method of claim 21, wherein the flow control device includes at least one additional conduit extending between the cavity and the external location.

27. The method of claim 26, wherein the conduits are arranged in parallel.

28. The method of claim 21, wherein engaging a flow control device with the housing comprises engaging a flow control device with the housing, wherein the at least one conduit comprises a single inlet port in fluid communication with the cavity defined by the housing, and a plurality of outlet ports each in fluid communication with the inlet port through respective channels extending from the inlet port.

29. The method of claim 28, wherein engaging a flow control device with the housing comprises engaging a flow control device with the housing, wherein the channels extend radially outward from the single inlet port such that the outlet ports are angularly spaced apart about the inlet port.

30. The method of claim 21, wherein the flow control device includes a first portion defining a single inlet port in fluid communication with the cavity defined by the housing, and a complementarily-configured second portion defining a plurality of outlet ports, and wherein the method comprises engaging the first and second portions to define a reservoir therebetween, and such that the outlet ports are each in fluid communication with the inlet port via the reservoir.

31. The method of claim 21, comprising engaging the flow control device with an output of a laser device so as to form at least one additional conduit in the flow control device.

32. The method of claim 21, comprising engaging the flow control device with an output of a laser device so as to seal the at least one conduit.

33. The method of claim 21, wherein engaging a flow control device with the housing comprises inserting a flow control device into the cavity defined by the housing.

34. An apparatus for draining aqueous humor from an eye for reducing or stabilizing intraocular pressure, the eye having an anterior chamber and including a cornea, a surrounding marginal limbus by which the cornea is continuous with a scleral layer and a conjunctival layer, and an external ocular surface of the eye under an eyelid, the apparatus comprising:

a tube extending between an inlet end and an outlet end, the inlet end being adapted to be in fluid communication with the anterior chamber of the eye, and the tube being adapted to direct a flow of aqueous humor from the anterior chamber and through the inlet end to the outlet end;

a flow control device operably engaged with the outlet end and configured to control the flow of the aqueous humor from the tube to a location external to the anterior chamber, the flow control device including at least one conduit extending between the outlet end and the external location, the at least one conduit configured to allow the flow of the aqueous humor from the cavity to the external location, an elongate portion of the at least one conduit formed from a flexible material configured to provide varying flow resistance as the aqueous humor continues to flow through the at least one conduit from the cavity to the external location, the flexible material defining a transverse cross-sectional area for the elongate portion of the at least one conduit, wherein in response to each of various increases in the intraocular pressure, the flexible material is configured to expand to respectively increase the transverse cross-sectional area along the elongate portion of the at least one conduit, the flow resistance decreasing as the cross-sectional area increases, and in response to each of various decreases in the intraocular pressure, the flexible material is configured to contract to respectively decrease the transverse cross-sectional area along the elongate portion of the at least one conduit, the flow resistance increasing as the cross-sectional area decreases;

a first filter device disposed in fluid communication between the inlet end of the tube and the flow control device, the first filter device being configured to filter contaminants from the aqueous humor prior to the flow control device; and a second filter device disposed in fluid communication with the flow control device, opposite to the outlet end of the tube from the flow control device, the second filter device being configured to filter contaminants from any backflow to the flow control device.

35. The apparatus of claim 34, wherein the first filter device is engaged with the outlet end of the tube, and wherein the flow control device is operably engaged with the first filter device such that the flow control device is removable or replaceable with respect thereto, so as to allow the first filter device to be removed or replaced.

36. The apparatus of claim 34, wherein the second filter device is engaged with the flow control device opposite to the first filter device, and wherein the flow control device is configured such that the second filter device is removable or replaceable with respect thereto, so as to allow the second filter device to be removed or replaced.

37. The apparatus of claim 34, further comprising a housing defining a cavity in fluid communication with the outlet end of the tube, the cavity being configured to receive the aqueous humor, and the housing being configured to operably engage the flow control device such that the flow control device regulates the flow of the aqueous humor from the cavity.

* * * * *